(12) United States Patent
Pardell-Pistiner et al.

(10) Patent No.: US 12,005,232 B1
(45) Date of Patent: Jun. 11, 2024

(54) METHODS AND DEVICES TO PREVENT OBSTRUCTIONS IN MEDICAL TUBES

(71) Applicant: CirculaTech LLC, Davie, FL (US)

(72) Inventors: Jake Tyler Pardell-Pistiner, Davie, FL (US); Stephen McClain, Nashville, TN (US); Rachel Malvagomes, Jefferson, LA (US); Kathleen Ana Gonzalez, Miami, FL (US); Carson Daniel Schaff, Fairhope, AL (US); Amirah Suleiman, Covington, GA (US); Nicholas Paul Bello, Sacramento, CA (US); Sara Budar, Jersey City, NJ (US); David Bradshaw Pearlstone, Monroe, CT (US)

(73) Assignee: CIRCULATECH LLC, Davie, FL (US)

( * ) Notice: Subject to any disclaimer, the term of this patent is extended or adjusted under 35 U.S.C. 154(b) by 517 days.

(21) Appl. No.: 17/222,562

(22) Filed: Apr. 5, 2021

Related U.S. Application Data

(63) Continuation of application No. 16/939,952, filed on Jul. 27, 2020, now Pat. No. 10,994,076.
(Continued)

(51) Int. Cl.
*A61M 5/168* (2006.01)
*A61M 39/02* (2006.01)
(Continued)

(52) U.S. Cl.
CPC .... *A61M 5/16831* (2013.01); *A61M 39/0208* (2013.01); *A61M 39/10* (2013.01); *A61M 39/24* (2013.01)

(58) Field of Classification Search
CPC .... A61M 5/16831; A61M 2005/16863; A61M 5/168; A61M 5/14; A61M 2005/1403; A61M 39/02; A61M 39/0208; A61M 39/10; A61M 39/24; A61M 1/00; A61M 1/0023; A61M 1/0039; A61M 1/0031; A61M 1/0058; A61M 1/0064; A61M 1/008;
(Continued)

(56) References Cited

U.S. PATENT DOCUMENTS 3,434,775 A 3/1969 Gosselin
3,807,390 A 4/1974 Ostrowski
(Continued)

*Primary Examiner* — Jason E Flick
(74) *Attorney, Agent, or Firm* — Husch Blackwell LLP; Bryan D. Stewart

(57) ABSTRACT

In various embodiments, a drainage device includes an inner lumen configured for draining fluid from a target site and one or more outer lumens for transmitting dilution fluid to the inner lumen. According to one embodiment, the drainage device includes one or more eyelets and/or a distal opening through which the fluid from the target site enters the inner lumen. In one or more embodiments, the dilution fluid is transmitted to the inner lumen through one or more ports that may output the dilution fluid directly into the inner lumen or into the eyelet. According to one embodiment, as the fluid from the target site flows through the drainage device, the dilution fluid reduces clotting processes such that formation of blockages within the inner lumen is prevented or at least reduced. In some embodiments, the dilution fluid is substituted with, or provided in addition to, pharmaceutical solutions or other infusions.

10 Claims, 25 Drawing Sheets

Related U.S. Application Data

(60) Provisional application No. 62/878,705, filed on Jul. 25, 2019.

(51) Int. Cl.
*A61M 39/10* (2006.01)
*A61M 39/24* (2006.01)

(58) Field of Classification Search
CPC ............... A61M 1/0084; A61M 25/00; A61M 2025/0004; A61M 25/0017; A61M 25/0021; A61M 25/0023; A61M 2025/0039; A61M 25/0043; A61M 25/0067; A61M 25/0068; A61M 25/007; A61M 27/00
See application file for complete search history.

(56) References Cited

U.S. PATENT DOCUMENTS

| | | | |
|---|---|---|---|
| 3,847,483 A | 11/1974 | Shaw | |
| 3,863,641 A | 2/1975 | Popa | |
| 4,291,694 A | 9/1981 | Chai | |
| 4,487,475 A | 12/1984 | Ogawa | |
| 4,647,149 A | 3/1987 | McCartney | |
| 4,648,892 A | 3/1987 | Kittrell | |
| 4,694,832 A | 9/1987 | Ungerstedt | |
| 4,695,276 A | 9/1987 | Shinno | |
| 4,718,423 A | 1/1988 | Willis | |
| 4,755,175 A | 7/1988 | Nilsson | |
| 4,759,378 A | 7/1988 | Swendson | |
| 4,762,130 A | 8/1988 | Fogarty | |
| 4,776,340 A | 10/1988 | Moran | |
| 4,788,967 A | 12/1988 | Ueda | |
| 4,790,295 A | 12/1988 | Tashiro | |
| 4,795,434 A | 1/1989 | Kujawski | |
| 4,796,604 A | 1/1989 | Kawashima | |
| 4,813,400 A | 3/1989 | Washizuka | |
| 4,830,013 A | 5/1989 | Maxwell | |
| 4,871,229 A | 10/1989 | Tashiro | |
| 4,911,148 A | 3/1990 | Sosnowski | |
| 4,921,483 A | 5/1990 | Wijay | |
| 5,047,627 A | 9/1991 | Yim | |
| 5,048,524 A | 9/1991 | Bailey | |
| 5,188,618 A | 2/1993 | Thomas | |
| 5,263,928 A | 11/1993 | Trauthen | |
| 5,263,952 A | 11/1993 | Grace | |
| 5,318,518 A | 6/1994 | Plechinger | |
| 5,512,248 A | 4/1996 | Van | |
| 5,738,656 A | 4/1998 | Wagner | |
| 5,897,534 A | 4/1999 | Heim | |
| 6,132,415 A | 10/2000 | Finch | |
| 6,299,593 B1 | 10/2001 | Wakabayashi | |
| 6,428,498 B2 * | 8/2002 | Uflacker | A61M 1/85 606/171 |
| 6,749,574 B2 | 6/2004 | O'Keefe | |
| 7,029,467 B2 | 4/2006 | Currier | |
| 7,309,055 B1 | 12/2007 | Spiegel | |
| 7,381,190 B2 | 6/2008 | Sugrue | |
| 7,766,938 B2 | 8/2010 | McGurk | |
| 7,798,974 B2 | 9/2010 | Sirokman | |
| 7,857,757 B2 | 12/2010 | Schaff | |
| 7,878,983 B2 | 2/2011 | Karpiel | |
| 8,246,602 B2 | 8/2012 | Heruth | |
| D679,804 S | 4/2013 | White | |
| 8,435,226 B2 | 5/2013 | Navis | |
| 8,500,674 B2 | 8/2013 | DeFonzo | |
| 8,506,479 B2 | 8/2013 | Piskun | |
| 8,523,801 B2 | 9/2013 | Nash | |
| 8,562,555 B2 | 10/2013 | MacMahon | |
| 8,702,662 B2 | 4/2014 | Boyle | |
| 8,740,874 B2 | 6/2014 | Ravenscroft | |
| 8,905,922 B2 | 12/2014 | Makower | |
| 8,951,355 B2 | 2/2015 | Boyle | |
| 9,084,868 B2 | 7/2015 | Aaronson | |
| 9,265,913 B2 | 2/2016 | Fallin | |
| 9,314,599 B2 | 4/2016 | Karwoski | |
| 9,446,224 B2 | 9/2016 | Fallin | |
| 9,883,877 B2 | 2/2018 | Look | |
| 10,004,863 B2 | 6/2018 | Vazales | |
| 10,076,592 B2 | 9/2018 | Ehlert | |
| 10,149,963 B2 | 12/2018 | Fallin | |
| 10,258,543 B1 | 4/2019 | Huttner | |
| 10,471,189 B2 | 11/2019 | O'Keefe | |
| 2004/0092956 A1 | 5/2004 | Liddicoat | |
| 2004/0143227 A1 | 7/2004 | Rollin | |
| 2011/0288161 A1 | 11/2011 | Day | |
| 2012/0330196 A1 | 12/2012 | Nita | |
| 2013/0150701 A1 | 6/2013 | Budar | |
| 2013/0178790 A1 | 7/2013 | Tekulve | |
| 2013/0195996 A1 | 8/2013 | Looper | |
| 2014/0135717 A1 | 5/2014 | Hensler | |
| 2014/0249472 A1 | 9/2014 | Mulvihill | |
| 2015/0231361 A1 | 8/2015 | O'Keefe | |
| 2016/0001036 A1 | 1/2016 | Nickerson | |
| 2016/0375221 A1 | 12/2016 | Panotopoulos | |
| 2017/0042516 A1 | 2/2017 | Boyle | |
| 2017/0143880 A1 | 5/2017 | Luxon | |
| 2018/0042623 A1 | 2/2018 | Batiste | |
| 2018/0280593 A1 | 10/2018 | Lehmann | |
| 2018/0338714 A1 | 11/2018 | Bayon | |
| 2019/0151587 A1 | 5/2019 | Vazales | |
| 2019/0269851 A1 | 9/2019 | Panotopoulos | |
| 2020/0038563 A1 | 2/2020 | Boyle | |
| 2020/0046453 A1 | 2/2020 | Vazales | |
| 2020/0054803 A1 | 2/2020 | Kucklick | |

* cited by examiner

METHODS AND DEVICES TO PREVENT OBSTRUCTIONS IN MEDICAL TUBES

CROSS REFERENCE TO RELATED APPLICATIONS

This application is a continuation of U.S. patent application Ser. No. 16/939,952, filed Jul. 27, 2020, entitled "METHODS AND DEVICES TO PREVENT OBSTRUCTIONS IN MEDICAL TUBES", which claims the benefit of and priority to U.S. Patent Application No. 62/878,705, filed Jul. 25, 2019, entitled "METHODS AND DEVICES TO PREVENT OBSTRUCTIONS IN MEDICAL TUBES," which are incorporated herein by reference in their entireties.

TECHNICAL FIELD

The present systems, methods, and devices relate generally to drainage of fluids from a body cavity.

BACKGROUND

Thoracic catheters, also called chest tubes, are used for the drainage of blood, fluids, and air from the mediastinal or pleural chest cavities. Previous embodiments of thoracic catheters have demonstrated an undesirable buildup of materials within the catheter, which can lead to various complications. For example, coagulation of blood within the catheter can cause clogs leading to inadequate drainage. As another example, coagulated fluids may be deposited back to the chest cavity, which can cause complications including, but not limited to, internal clotting, blockages, and other issues which may be collectively classified under Retained Blood Syndrome (RBS).

As stated above, RBS can be induced during previous approaches to thoracic catheterization, for example, in instances where catheter blockages result in insufficient drainage. In such instances, blood may clot inside the patient and cannot be reabsorbed by the body. To address such complications, previous approaches include inserting vacuum powered chest tubes and maintaining a negative pressure for several days to remove this excess blood from the patient. When this blood enters the chest tube it may immediately begin to clot (e.g., due to contact with a foreign surface), which can gradually cause the chest tube to become occluded. Eventually, the chest tube may become substantially ineffective due to the increasing occlusion, thereby causing a multitude of complications including postoperative atrial fibrillation, hemothorax, fibrothorax, and cardiac tamponade. The current techniques for eliminating clogs, include milking or stripping the chest tubes. Such techniques are typically time and energy-intensive, and have demonstrated a lack of efficacy and safety. Furthermore, such approaches may be implemented reactively following blockage detection and, thus, may not actively preempt clot formation.

Therefore, there is a long-felt but unresolved need for a system or method that actively reduces the likelihood of blockage formation within chest tubes and other catheters.

BRIEF SUMMARY OF THE DISCLOSURE

Briefly described, and according to one embodiment, aspects of the present disclosure generally relate to blockage resistant devices and methods for using the same.

In at least one embodiment, the blockage resistant devices include, but are not limited to, drainage devices, such as chest tubes and catheters, and other devices insertable to a target site. In various embodiments, drainage devices include devices configured for closed, open, and active suction. According to one embodiment, the target site refers to a particular region of a body, such as, for example, a chest cavity. Non-limiting examples of target sites include, but are not limited to, veins and arteries, organs, such as lungs, and other portions of anatomy. In one or more embodiments, the blockage resistance of devices described herein is provided via one or more fluids that are passed through the device and prevent, or at least reduce, blockage forming processes, such as clotting.

In one or more embodiments, a blockage resistant drainage device includes a shaft including a substantially cylindrical shape. In at least one embodiment, the shaft includes an inner lumen that may be centrally located or positioned along an interior of a wall defining the shaft. In various embodiments, the shaft includes a proximal end and a distal end opposite the proximal end. As used herein, "distal" generally refers to a direction towards a target site (e.g., a patient). As used herein, "proximal" generally refers to a direction opposite a distal direction and towards a user of the described devices.

According to one embodiment, a variable vacuum source may be connected near the proximal end and, upon activation, may generate a negative pressure within the inner lumen that draws fluid at a target site into the drainage device via the distal end. In at least one embodiment, the distal end is open such that the fluid may enter the inner lumen. In some embodiments, the shaft includes one or more eyelets that connect the inner lumen to the target site such that the fluid therefrom enters the inner lumen through the one or more eyelets (in addition to, or instead of, an opening at the distal end).

In various embodiments, the shaft includes one or more outer lumens that may be formed into the wall. In at least one embodiment, the outer lumen includes an inlet (e.g., near a proximal end) through which fluid is transmitted into the outer lumen. The fluid may include, for example, isotonic, hypertonic, or hypotonic buffer solutions and other fluids for reducing blockage formation or for providing a desired treatment at the target site. The buffer solutions may include, but are not limited to, saline solution, Ringer's solution, phosphate-buffered saline solution, and aqueous dextrose solutions (e.g., 5% dextrose in water, D5W). In one or more embodiments, the fluid includes one or more medications, including, but not limited to, anticoagulants, antibiotics, antifungals, antivirals, thrombolytics, and mucolytics, such as acetylcysteine.

According to one embodiment, the outer lumen includes one or more ports that connect the outer lumen to the inner lumen such that the dilution fluid may pass from the outer lumen into the inner lumen. As used herein, "port" generally refers to any structure or mechanism that passes fluids from an outer lumen to inner lumen. As such, a port may take many forms as discussed herein. In one or more embodiments, the one or more ports are connected to a wall of an eyelet such that the dilution fluid is transmitted into the inner lumen by passing through the eyelet. In one example, as blood enters the eyelet, an anticoagulant solution from the outer lumen mixes with and dilutes the blood to reduce the prevalence of clotting processes that may otherwise lead to clot formation and the partial or total occlusion of the inner lumen.

According to one embodiment, an attachment device is provided for connecting the outer lumen to one or more fluid sources. In at least one embodiment, the attachment device is configured to slide over and align with the one or more inlets of the outer lumen. In one or more embodiments, the attachment device includes one or more inputs that are connected to the one or more fluid sources. According to one embodiment, the input includes a luer lock fitting or other standard fitting attachable to standard medical tubing and other equipment. In various embodiments, the attachment device includes a chamber to which the input is connected and from which the dilution fluid enters the one or more inlets. In some embodiments, the attachment device includes a second chamber that is separated from the first chamber and a second input that is separated from the first input. In one or more embodiments, the first chamber is aligned over a first inlet to a first outer lumen and the second chamber is aligned over a second inlet to a second outer lumen that is separated from the first outer lumen. In at least one embodiment, the multiple chambers and inputs allow for different fluids to be provided to the drainage device simultaneously or at predetermined time points.

According to a first aspect, a blockage resistant drainage device comprising: A) a generally cylindrical body forming a longitudinal axis between a proximal end and a distal end; B) an inner lumen formed within the generally cylindrical body; C) an outer lumen formed and within the generally cylindrical body; D) at least one eyelet located near the distal end and extending from an exterior surface of the generally cylindrical body to the inner lumen for draining fluid from the chest of a patient, the at least one eyelet comprising: 1) a first substantially circular opening at the exterior surface; and 2) a second substantially circular opening at a point of entry of the inner lumen, wherein: i) a diameter of the second substantially circular opening is smaller than a diameter of the first substantially circular opening; and ii) the at least one eyelet interfaces with the outer lumen such that an dilution fluid may pass through the outer lumen along the longitudinal axis from a point near the proximal end and into the inner lumen via the at least one eyelet.

According to a second aspect, the blockage resistant drainage device of the first aspect or any other aspect, wherein the at least one eyelet interfaces with the outer lumen between the first substantially circular opening and the second substantially circular opening.

According to a third aspect, the blockage resistant drainage device of the second aspect or any other aspect, wherein: A) the at least one eyelet comprises an eyelet wall between the first substantially circular opening and the second substantially circular opening; and B) the eyelet wall forms an opening to the outer lumen, allowing the dilution fluid to pass from the outer lumen to the inner lumen via the at least one eyelet.

According to a fourth aspect, the blockage resistant drainage device of the third aspect or any other aspect, wherein the inner lumen is configured to be operatively connected to a vacuum system.

According to a fifth aspect, the blockage resistant drainage device of the fourth aspect or any other aspect, wherein the outer lumen is configured to be operatively connected to a pump at the point near the proximal end for pumping the dilution fluid to the at least one eyelet.

According to a sixth aspect, the blockage resistant drainage device of the fourth aspect or any other aspect, wherein the outer lumen is configured to be operatively connected to a syringe at the point near the proximal end for pumping the dilution fluid to the at least one eyelet.

According to a seventh aspect, the blockage resistant drainage device of the fourth aspect or any other aspect, wherein the blockage resistant drainage device further comprises a luer lock comprising a one-way valve at the point near the proximal end for connecting the pump to the outer lumen.

According to an eighth aspect, the blockage resistant drainage device of the seventh aspect or any other aspect, wherein the diameter of the first substantially circular opening is about 1-50 mm.

According to a ninth aspect, the blockage resistant drainage device of the eighth aspect or any other aspect, wherein the at least one eyelet is one of a plurality of eyelets extending from the exterior surface of the generally cylindrical body to the inner lumen for draining fluid from the chest of the patient.

According to a tenth aspect, the blockage resistant drainage device of the ninth aspect or any other aspect, wherein a second eyelet of the plurality of eyelets comprises a second eyelet wall defining an opening to the outer lumen, allowing the dilution fluid to pass from the outer lumen to the inner lumen via the second eyelet.

According to an eleventh aspect, a blockage resistant drainage device comprising: A) a generally cylindrical body forming a longitudinal axis between a proximal end and a distal end; B) an inner lumen formed within the generally cylindrical body; C) a plurality of outer lumens formed and within the generally cylindrical body; D) a plurality of eyelets extending from an exterior surface of the generally cylindrical body to the inner lumen for draining fluid from the chest of a patient, each of the plurality of eyelets comprising: 1) a first substantially circular opening at the exterior surface; 2) a second substantially circular opening at a point of entry of the inner lumen, wherein a diameter of the second substantially circular opening is smaller than a diameter of the first substantially circular opening; and 3) an eyelet wall between the first substantially circular opening and the second substantially circular opening defining an opening to at least one outer lumen of the plurality of outer lumens such that an dilution fluid may pass through the at least one outer lumen along the longitudinal axis from a point near the proximal end and into the inner lumen.

According to a twelfth aspect, the blockage resistant drainage device of the eleventh aspect or any other aspect, wherein the inner lumen is configured to be operatively connected to a vacuum system.

According to a thirteenth aspect, the blockage resistant drainage device of the twelfth aspect or any other aspect, wherein the plurality of outer lumens are configured to be operatively connected to a pump at the point near the proximal end for pumping the dilution fluid to the plurality of eyelets.

According to a fourteenth aspect, the blockage resistant drainage device of the twelfth aspect or any other aspect, wherein the outer lumen is configured to be operatively connected to a syringe at the point near the proximal end for pumping the dilution fluid to the at least one eyelet According to a fifteenth aspect, the blockage resistant drainage device of the fourteenth aspect or any other aspect, wherein the blockage resistant drainage device further comprises a luer lock comprising a one-way valve at the point near the proximal end for connecting the pump to the plurality of outer lumens.

According to a sixteenth aspect, the blockage resistant drainage device of the fourteenth aspect or any other aspect, wherein the diameter of the first substantially circular opening is about 1-50 mm.

According to a seventeenth aspect, the blockage resistant drainage device of the fourteenth aspect or any other aspect, wherein a particular eyelet of the plurality of eyelets comprises a particular eyelet wall between a particular first substantially circular opening and a particular second substantially circular opening defining a particular opening to a particular outer lumen of the plurality of outer lumens such that the dilution fluid may pass through the particular outer lumen along the longitudinal axis from the point near the proximal end and into the inner lumen.

According to an eighteenth aspect, the blockage resistant drainage device of the seventeenth aspect or any other aspect, wherein a specific eyelet of the plurality of eyelets comprises a specific eyelet wall between a specific first substantially circular opening and a specific second substantially circular opening defining a specific opening to a specific outer lumen of the plurality of outer lumens such that the dilution fluid may pass through the specific outer lumen along the longitudinal axis from the point near the proximal end and into the inner lumen.

According to a nineteenth aspect, the blockage resistant drainage device of the eighteenth aspect or any other aspect, wherein the particular outer lumen and the specific outer lumen are the same outer lumen.

According to a twentieth aspect, the blockage resistant drainage device of the eighteenth aspect or any other aspect, wherein the particular outer lumen and the specific outer lumen are different outer lumens.

According to a twenty-first aspect, a method of using a blood clot resistant chest tube comprising: A) installing a distal end of a blockage resistant drainage device into the chest of a patient, the blockage resistant drainage device comprising: 1) a generally cylindrical body forming a longitudinal axis between a proximal end and the distal end; 2) an inner lumen formed within the generally cylindrical body; 3) an outer lumen formed and within the generally cylindrical body; and 4) at least one eyelet extending from an exterior surface of the generally cylindrical body to the inner lumen for draining fluid from the chest of a patient, the at least one eyelet comprising: i) a first substantially circular opening at the exterior surface; ii) a second substantially circular opening at a point of entry of the inner lumen, a diameter of the second substantially circular opening is smaller than a diameter of the first substantially circular opening; iii) an eyelet wall between the first substantially circular opening and the second substantially circular opening; and iv) an opening to the outer lumen defined by the eyelet wall; and allowing the dilution fluid to pass from the outer lumen to the inner lumen via the at least one eyelet; and B) causing an dilution fluid to pass through the outer lumen along the longitudinal axis from a point near the proximal end and into the inner lumen via the opening defined by the eyelet wall, thereby mixing the dilution fluid with blood of the patient as blood from the patient passes through the at least one eyelet.

These and other aspects, features, and benefits of the claimed devices, systems, and methods will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
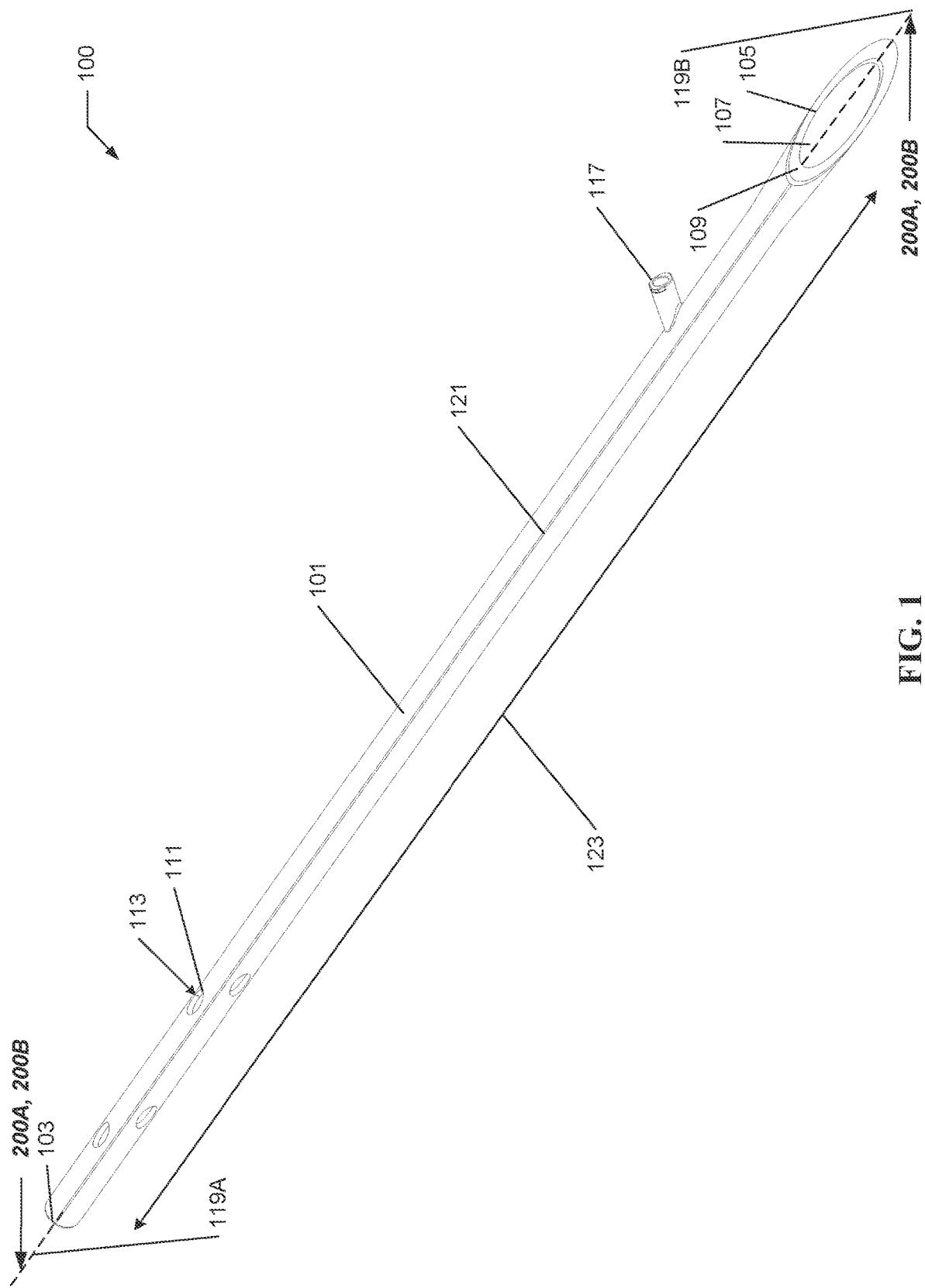
FIG. 1 is a perspective view of an exemplary drainage device, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to blockage resistant drainage devices and methods for using the same. In at least one embodiment, a blockage resistant drainage device is configured to be inserted at a target site and drain fluids therefrom into an inner lumen (e.g., under negative pressure). According to one embodiment, the drainage device demonstrates blockage resistance via one or more outer lumens that transmit dilution fluid to the inner lumen, which may reduce blockage-processes such as clotting. In some embodiments, the drainage device is an infusion device for delivering pharmaceutical solutions or other fluids to a target site or to fluids drained therefrom.

Exemplary Embodiments

FIG. 1 is a perspective view of a drainage device 100, according to one embodiment. In various embodiments, the drainage device 100 includes a shaft 101 between a distal end 103 and a proximal end 105. According to one embodiment, the distal end 103 and/or proximal end 105 are openings through which fluids or instruments may be passed. In one example, the distal end 103 is an opening through which blood from a target site enters the drainage device 100. In another example, the proximal end 105 is an opening sized such that tubing may be slid over or into the opening to connect the drainage device 100 to a vacuum source.

In one or more embodiments, the shaft 101 includes a substantially cylindrical shape. In some embodiments, the shaft 101 is curved or angled. In one example, the shaft 101 includes a curve that deflects the angle of the shaft 101 by about 0-180 degrees, about 5-45 degrees, about 45-90 degrees, about 90 degrees, about 90-135 degrees, or about 135-180 degrees between the distal end 103 and the proximal end 105. In various embodiments, the shaft 101 includes one or more materials, including, but not limited to, polyvinyl chloride (PVC), polyurethane, silicone, biocompatible semi-elastic polymers, and other suitable materials. In one or more embodiments, the shaft 101 is substantially transparent such that a user may observe fluid passing through the shaft 101, for example, to assess blockage formation and fluid properties. In some embodiments, outer lumens and inner lumens include differing color schemes or coatings that allow for fluids flowing in the outer lumens to be differentiated from fluids flowing in the inner lumen. For example, an inner lumen includes a lower level of transparency than an outer lumen, thereby allowing for an observer to differentiate between fluids flowing through the outer lumens and fluids flowing through the inner lumens (e.g., which may appear darker in comparison). In at least one embodiment, the shaft 101 includes radiopaque material, such as barium sulfate, that renders the drainage device 100 (or a portion thereof) detectable by various imaging techniques, such as X-ray.

In one or more embodiments, the shaft 101 includes an inner lumen 107 that extends between the distal end 103 and the proximal end 105. In at least one embodiment, a wall 109 defines the inner lumen 107. In various embodiments, the shaft 101 includes one or more eyelets 111 that extend through the wall 109 to the inner lumen 107. According to one embodiment, the eyelet 111 includes a void connecting the inner lumen 107 to the region external to the drainage device 100. For example, upon insertion to a target site, the eyelet 111 connects the inner lumen 107 to the body such that blood drains into the drainage device 100 at least partially through the eyelet 111. According to one embodiment, the eyelet 111 includes a substantially elliptical shape. In alternate embodiments, the eyelet 111 includes one or more shapes including, but not limited to, circles, quadrilaterals, other polygons, or any suitable shape.

In one or more embodiments, a portal 113 connects an outer lumen 201 (see FIG. 2) to the eyelet 113. In at least one embodiment, fluids transmitted through the outer lumen exit through the portal 113 and into the eyelet 111. In one example, saline solution is pumped through the portal 113 and contacts blood draining through the eyelet 111 and into the drainage device 100. In this example, the saline solution dilutes the incoming blood to potentially reduce the likelihood of a blockage forming within the inner lumen 107 (e.g., due to clot formation). In some embodiments, the portal 113 connects the inner lumen 107 to the outer lumen 201 such that fluid may be transmitted directly from the outer lumen 201 to the inner lumen 107. According to one embodiment, the drainage device 100 includes a port 117 that is connected to one or more outer lumens 201 such that fluid injected at the port 117 is transmitted to the one or more outer lumens 201.

In at least one embodiment, the drainage device 100 is configured for insertion to a target site, such as a chest cavity, and for facilitating drainage of fluids, such as blood, from the target site via vacuum forces. According to one embodiment, a vacuum source is connected to the inner lumen 107 at the proximal end 105 and provides a vacuum source that directs fluid external to the drainage device 100 into the inner lumen 107. In various embodiments, fluids enter the drainage device 100 through an opening at the distal end 103 and/or through one or more eyelets 111. In at least one embodiment, the proximal end 105 is configured for connection to one or more apparatuses or devices including, but not limited to, vacuum apparatuses, collection devices, and pumps, such as infusion pumps. In one example, the distal end 103 (e.g., and a desired length of the shaft 101) is inserted into a chest cavity and, upon activation of a connected vacuum apparatus, the drainage device 100 suctions blood from the chest cavity through the eyelets 111 and/or the distal end 103, and the blood is transmitted into a connected collection device.

In one or more embodiments, the drainage device 100 includes indicia 121 that includes one or more radiopaque materials, such as barium sulfate, that render the indicia 121 observable via one or more imaging modes, such as X-ray. In one example, the indicia 121 allows for the position of the drainage device 100 to be monitored at a target site within a body.

In at least one embodiment, the drainage device 100 includes a length 123 between the distal end 103 and proximal end 105. In various embodiments, the length 121 measures about 1-300 cm, about 1-25 cm, about 25-50 cm, about 50-75 cm, about 75-100 cm, about 100-125 cm, about 125-150 cm, about 150-175 cm, about 175-200 cm, about 200-225 cm, about 225-250 cm, about 250-275 cm, or about 275-300 cm.

According to one embodiment, a longitudinal axis 119A, 119B bisects the drainage device 100. In one or more embodiments, the longitudinal axis 119A, 119B defines various cross-sections described herein and as shown in FIGS. 2A-B.

Figure 2A:
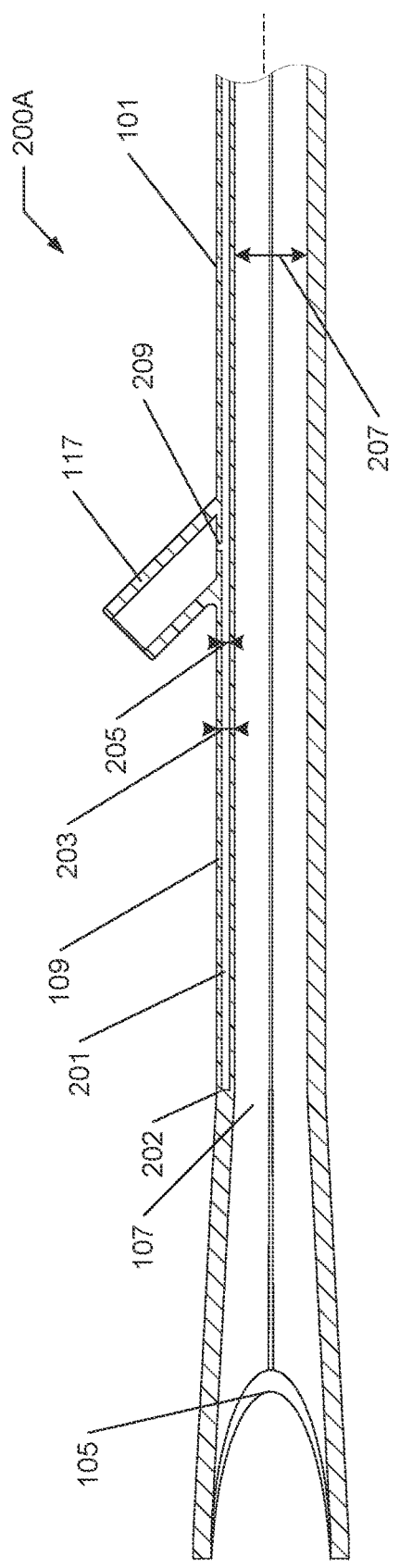
FIGS. 2A-B are cross-sectional views of an exemplary drainage device, according to one embodiment of the present disclosure.
Figure 2B:
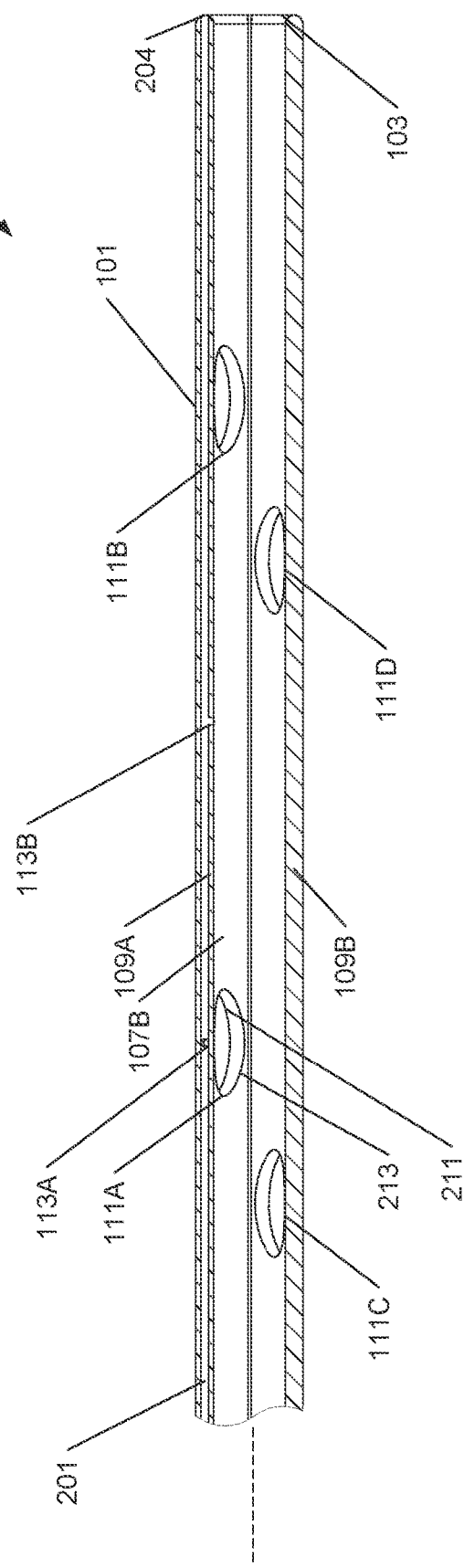

FIG. 2A shows a cross-section 200A of the drainage device 100, according to one embodiment. In one or more embodiments, the cross-section 200A includes a section of the drainage device 100 near the proximal end 105 and the cross-section 200B (see FIG. 2B) includes a section of the drainage device near the distal end 103.

In one or more embodiments, the wall 109 includes one or more outer lumens 201. For example, the wall 109 includes four outer lumens 201 arranged in a radial pattern within the wall 109. In various embodiments, the number of outer lumens 201 is between about 1-20. According to one embodiment, the outer lumen 201 is defined by a void within the wall 109 that extends from an area near the proximal end 105, along the length of the shaft 101, and generally to a point or area near the distal end 103. In some embodiments, the outer lumen 201 extends between an outer lumen proximal end 202 and an outer lumen distal end 204. In one example, the outer lumen proximal end 202 corresponds to a region of the outer lumen 201 at which an inlet 209 is connected to the outer lumen 201. In another example, the outer lumen distal end 204 is aligned with the distal end 103. In an alternate example, the outer lumen distal end 204 is aligned with an eyelet 111 or port 113.

In one or more embodiments, the outer lumen 201 is configured for transmitting fluids and/or instruments, such as sensor probes, into the inner lumen 107, the eyelets 111, and/or to a target site. In one example, the outer lumen 201 transmits dilution fluid to the inner lumen 107 to reduce clotting processes that may occur therein. In some embodiments, the outer lumen 201 is configured to transmit fluid at a particular fluid:blood ratio that may measure about 100:1, about 50:1, about 25:10, about 10:1, about 5:1, or about 2:1, about 1:1, about 1:10, about 1:100, about 1:1000, or about 1:10000. According to one embodiment, multiple eyelets 111 are connected to each outer lumen 201. In some embodiments, a single eyelet 111 is connected to each outer lumen 201. In one example, to remove blockages and reduce the likelihood of blockage formation during drainage, the outer lumen 201 transmits saline solution through one or more ports 113 and into the inner lumen 107. In this example, the saline solution dilutes blood passing through the inner lumen 107 such that clotting processes are prevented from occurring and/or coagulation of blood does not propagate to a point precipitating a blockage.

In various embodiments, the wall 109 includes a thickness 203 that measures about 0.01-10.0 mm, about 0.01-0.1 mm, about 0.1-1.0 mm, about 1.0-2.0 mm, about 2.0-3.0 mm, about 3.0-4.0 mm, about 4.0-5.0 mm, about 5.0-6.0 mm, about 6.0-7.0 mm, about 7.0-8.0 mm, about 8.0-9.0 mm, or about 9.0-10.0 mm. In one or more embodiment, the outer lumen 201 includes a diameter 205 that measures about 0.01-10.0 mm, about 0.01-0.1 mm, about 0.1-1.0 mm, about 1.0-2.0 mm, about 2.0-3.0 mm, about 3.0-4.0 mm, about 4.0-5.0 mm, about 5.0-6.0 mm, about 6.0-7.0 mm, about 7.0-8.0 mm, about 8.0-9.0 mm, or about 9.0-10.0 mm. In some embodiments, the diameter 205 tapers near the distal end 103. According to one embodiment, the drainage device 100 includes two or more outer lumens of different diameters. As one example, the drainage device 100 includes a first outer lumen and a second outer lumen. In this example, the first outer lumen includes a first diameter that is greater than a second diameter of the second outer lumen. In at least one embodiment, the inner lumen 107 includes a diameter 207 that measures about 0.01-50.0 mm, about 0.01-0.1 mm, about 0.1-1.0 mm, about 1.0-5.0 mm, about 5.0-10.0 mm, about 10.0-20.0 mm, about 20.0-30.0 mm, about 30.0-40.0 mm, or about 40.0-50.0 mm.

Figure 11:
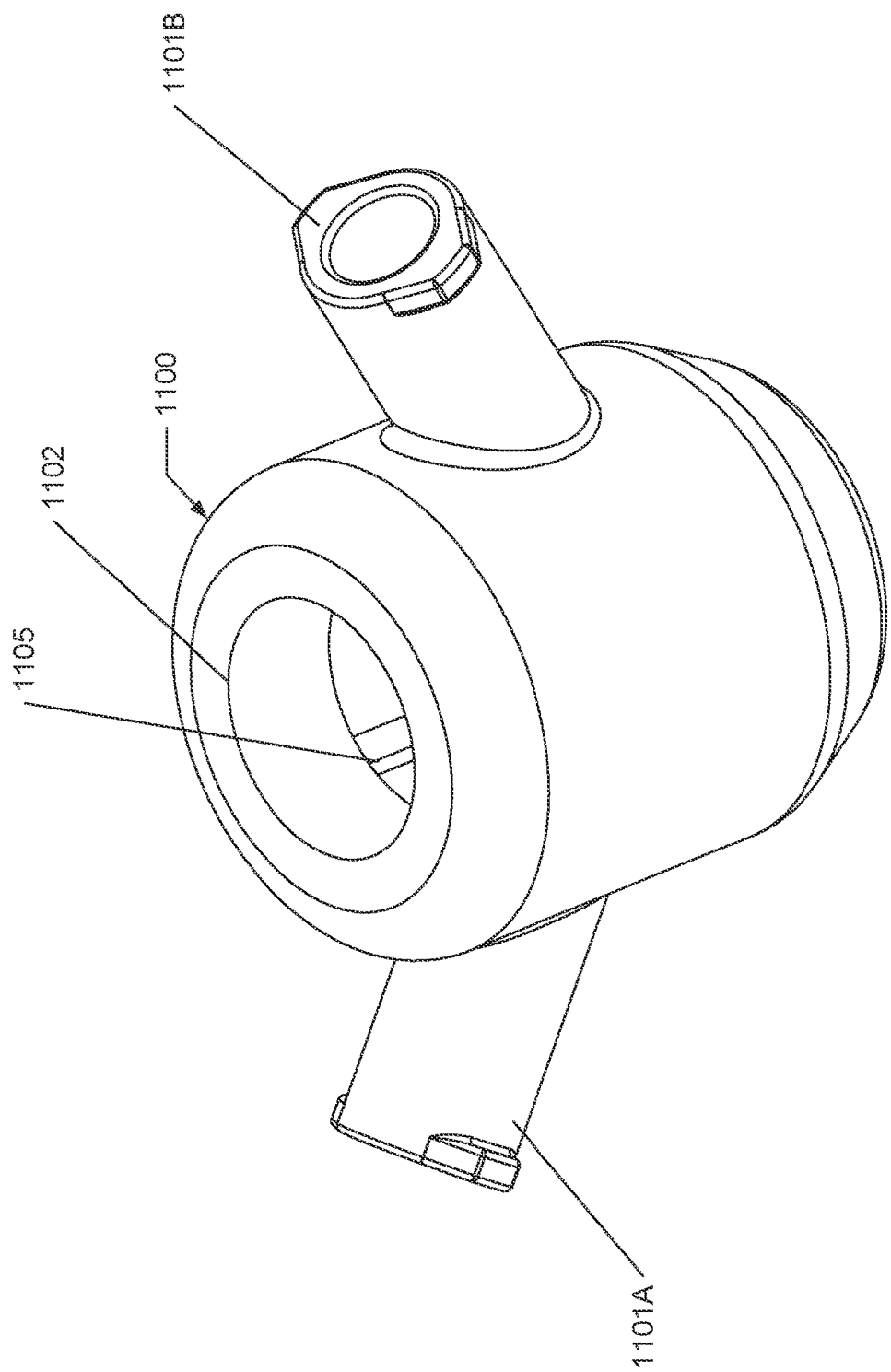
FIG. 11 is a perspective view of an exemplary attachment device, according to one embodiment of the present disclosure.

According to one embodiment, the port 117 is connected to an inlet 209 that opens into the outer lumen 201. In some embodiments, a port is connected to multiple inlets. In various embodiments, two or more ports 117 are included and each port 117 is connected to a different inlet 209 opening to different outer lumens 201. In alternate embodiments, the drainage device 100 does not include the port 117 and, instead, an attachment device is fitted over the shaft 101 and configured to transmit fluid through the inlet 209. Non-limiting examples of attachment devices include, but are not limited, an attachment device 300 (FIG. 3) and an attachment device 1100 (FIG. 11). In at least one embodiment, the outer lumen 201 extends past the inlet 209 (e.g., as shown in FIG. 2A). In alternate embodiments, the outer lumen 201 initiates at a point along the shaft 101 that is aligned with the inlet 209.

FIG. 2B shows a cross-section 200B of the drainage device 100, according to one embodiment. In at least one embodiment, the cross-section 200B is a section of the drainage device 100 located near the distal end 103. According to one embodiment, the distal end 103 is open such that fluid may enter through the distal end 103 and into the inner lumen 107.

In various embodiments, the eyelet 111A includes a first opening 211 and a second opening 213 distanced from and generally opposite the first opening 211. In at least one embodiment, the first opening 211 is open to the environment exterior to the drainage device 100, such as a body cavity, and the second opening 213 is open to the inner lumen 107. According to one embodiment, fluid flows from the outer lumen 201 into the port 113A and flows from the port 113A into the eyelet 111A (e.g., passing through the wall 109, passage not shown). In at least one embodiment, the fluid flows into the eyelet 111A via a void (e.g., a portion of the port 113A not shown in FIG. 2B) between the first opening 211 and second opening 213. In various embodiments, from the eyelet 111A, the fluid flows into the inner lumen 107. In some embodiments, edges of the first opening 211 and/or second opening 213 are rounded or chamfered, for example, to reduce a likelihood of piercing of cutting tissue at a target site.

In at least one embodiment, the outer lumen 201 extends to the distal end 103 and a port is positioned at the outer lumen distal end 204. In one example, dilution fluid exiting from the port positioned at the outer lumen distal end 204 is directed at blood near the distal end 103 such that the incoming blood is diluted prior to entering the drainage device 100.

In one or more embodiments, the shaft 101 includes multiple eyelets 111A, 111B, 111C, 111D that are connected to the outer lumen 201 such that fluid from the outer lumen 201 is transmittable to the eyelets 111A, 111B, 111C, 111D. In some embodiments, each eyelet 111A, 111B, 111C, 111D is connected to a different outer lumen (e.g., outer lumen 201). In various embodiments, a particular outer lumen 201 is connected to a first subset of eyelets 111 and a second outer lumen is connected to a second subset of eyelets 111 that excludes the first subset.

According to one embodiment, the eyelets 111A, 111B, 111C, 111D direct fluid from the outer lumen 201 and fluid from an external environment, such as a body cavity, into the inner lumen 107. In various embodiments, the eyelet 111 extends through the wall 109A and the outer lumen 201 and into the inner lumen 107 such that fluid from the external environment enters the eyelet 111 and mixes with fluid from the outer lumen 201 before the fluid mixture flows into the inner lumen 107 (e.g., where additional mixing and/or dilution may occur). According to one embodiment, the transmission of fluid from the outer lumen 201 into the eyelet 111A reduces blockage formation at the eyelet 111A and/or provides for more immediate dilution of other fluids, such as blood, entering the eyelet 111A.

In some embodiments, the eyelet 111D is a channel of constant diameter that is formed as a "cut" through the wall 109A. In one example, an eyelet includes a first opening on an exterior-facing side of a drainage device wall and includes a second opening on an interior-facing (e.g., inner lumen—facing) side of the wall. Continuing this example, via an outer lumen, the first and second openings form a channel through the wall. In this same example, the second opening is located on the shaft at a point closer to a proximal end of the drainage device than a second point at which the first opening is located, thereby forming an angled channel oriented towards the proximal end.

According to one embodiment, the eyelets 111A, 111B, 111C, 111D are arranged to allow for drainage into the drainage device 100 to occur from multiple directions, which may be desirable in instances where a particular eyelet 111 is occluded. In one example, the eyelets 111A, 111B, 111C, 111D are arranged in a helical or other spiral pattern along the length of the shaft 101. In another example, the eyelets 111A, 111B, 111C, 111D are arranged in a radial pattern to provide for increased drainage (e.g., in 360 degrees). In at least one embodiment, the outer lumen 201 is connected to the eyelet 111A via the port 113A. In one or more embodiments, the port 113A includes a channel (not shown) passing from the outer lumen 201, through the wall 109A, and into the eyelet 111A. In various embodiments, a subset of ports are connected to eyelets and a second subset of ports are connected directly to the inner lumen. In one example, the port 113A is connected to the eyelet 113A and the port 113B is connected to the inner lumen 107.

According to one embodiment, a port 113 is arranged along the length of the shaft 101 such that the port 113 transmits fluid toward an opposing section of the wall 109 within the inner lumen 107. For example, the port 113B is arranged such that fluid transmitted thereby is directed at the wall 109B. In this example, the fluid forms a spray upon impacting the wall 109B, which potentially increases the distribution of the fluid and improves a rate at which blood passing through the inner lumen 107 is diluted by the fluid. In some embodiments, a port is angled such that fluid transmitted thereby enters an inner lumen at a particular angle. In one example, a port is angled toward a proximal end of a drainage device. In an alternate example, the port is angled toward a distal end of the drainage device.

Figure 3:
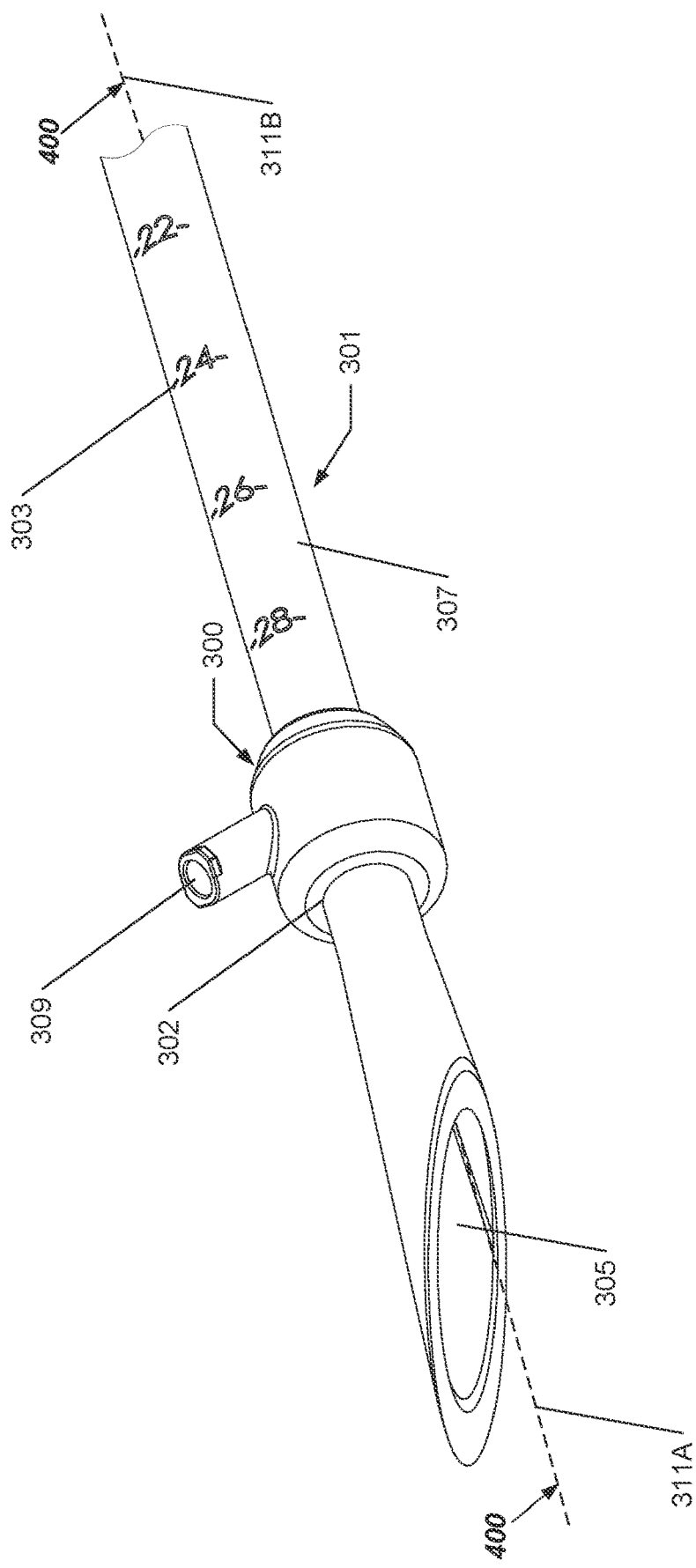
FIG. 3 is a perspective view of an exemplary attachment device, according to one embodiment of the present disclosure.

FIG. 3 is a perspective view of an attachment device 300, according to one embodiment. In at least one embodiment, the attachment device 300 is attached to a drainage device 301. In various embodiments, the attachment device 300 includes a central portion 302 (FIG. 5) through which the drainage device 301 is passed. In some embodiments, the drainage device 301 is generally similar to the drainage device 100 (see FIG. 1, FIGS. 13-22). In various embodiments, the attachment device 300 includes one or more materials, including, but not limited to, biocompatible plastics that may not significantly compromise a quality fluid with which the plastics may contact. In at least one embodiment, various elements of the drainage device 300 discussed in the foregoing description are demonstrated by the drainage device 100.

According to one embodiment, the drainage device 301 includes indicia 303 that indicate an inserted depth of the drainage device 301 and/or a volume of fluid within an inner lumen 305. In one or more embodiments, the indicia 303 include one or more radiopaque materials, such as barium sulfate, that render the indicia 303 detectable through imaging modes such as X-ray. In at least one embodiment, a plurality of indicia 303 are located along a shaft 307 at predetermined increments.

In various embodiments, the attachment device 300 is configured to transmit one or more fluids to the drainage device 300. Non-limiting examples of the one or more fluids include, but are not limited to, dilution fluids, such as a heparin solution, saline, contrast agents, and pharmaceuticals. In at least one embodiment, the attachment device 300 allows one or more instruments, such as sensors or other medical devices, to be inserted into the drainage device 301. In at least one embodiment, the attachment device 300 includes an input 309 that may be connected to one or more fluid sources for supplying the one or more fluids. According to one embodiment, the input 309 includes a luer lock connector or other standard fitting. In some embodiments, the input 309 includes tubing (not shown) that allows the input 309 to be connected to a nearby fluid source.

According to one embodiment, the attachment device 300 is sized to slide over the drainage device 301 and maintain a position along a shaft 307 thereof. In one example, the attachment device 300 is sized such that frictional forces are generated at the interface between the shaft 303 and the attachment device 300, the frictional forces being sufficient for securing and maintaining a position of the attachment device 300.

Figure 4:
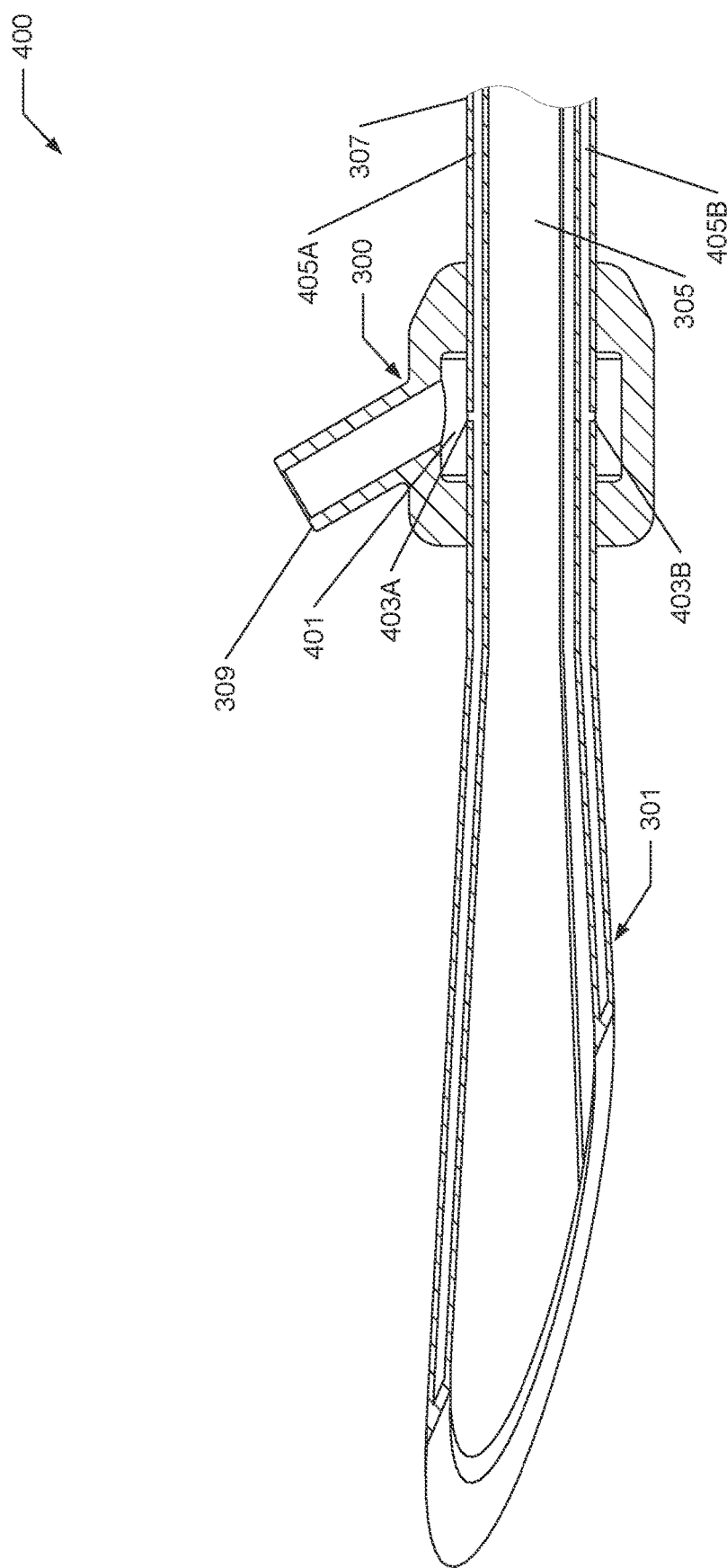
FIG. 4 is a cross-sectional view of an exemplary attachment device, according to one embodiment of the present disclosure.

In various embodiments, a longitudinal axis 311A, 311B bisects the attachment device 300 and drainage device 301, and defines a cross-section 400 (FIG. 4).

FIG. 4 shows a cross-section 400 of the attachment device 300, according to one embodiment. In at least one embodiment, the input 309 is connected to a chamber 401 such that fluid from the input 309 flows into the chamber 401 and to one or more inlets 403A, 403B. In various embodiments, upon the attachment device 300 being attached to the drainage device 300, the chamber 401 is aligned over inlets 403A, 403B that provide openings through the shaft 307 to outer lumens 405A, 405B. In alternate embodiments (not shown), the inlets 403A, 403B provide openings to an inner lumen (e.g., inner lumen 305). In one or more embodiments, the fluid transmitted through the attachment device 300 passes from the chamber 401 into the inlets 403A, 403B and into the outer lumens 405A, 405B, which may further transmit the fluid to the inner lumen 305.

According to one embodiment, the chamber 401 is sealed against leakage due to the sizing of the attachment device 300. In some embodiments, the attachment device 300 includes rubberized seals that interface with the shaft 307 to prevent leakage.

Figure 5:
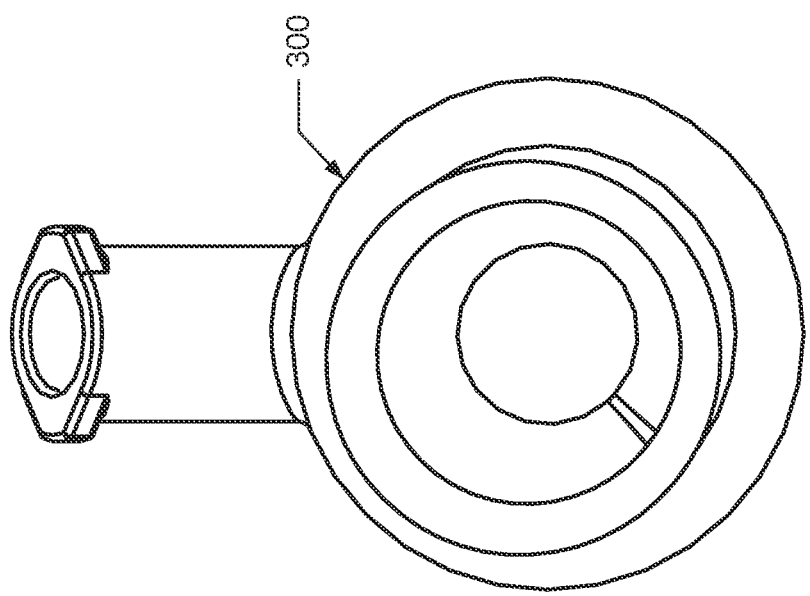
FIG. 5 is a top view of an exemplary attachment device, according to one embodiment of the present disclosure.

FIG. 5 is a top view of an attachment device 300, according to one embodiment.

Figure 6:
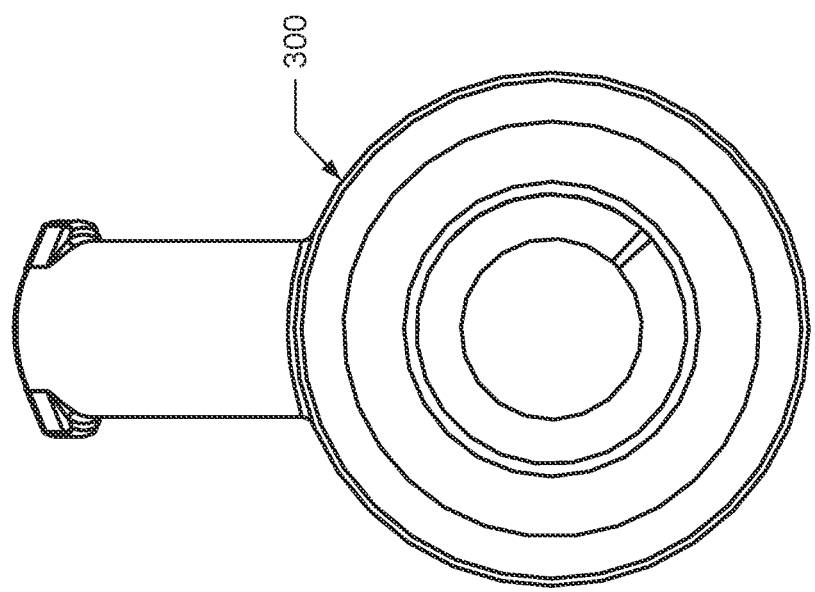
FIG. 6 is a bottom view of an exemplary attachment device, according to one embodiment of the present disclosure.

FIG. 6 is a bottom view of an attachment device 300, according to one embodiment.

Figure 7:
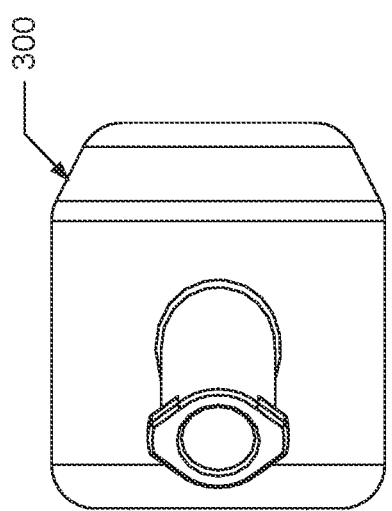
FIG. 7 is a front view of an exemplary attachment device, according to one embodiment according to one embodiment of the present disclosure.

FIG. 7 is a front view of an attachment device 300, according to one embodiment.

Figure 8:
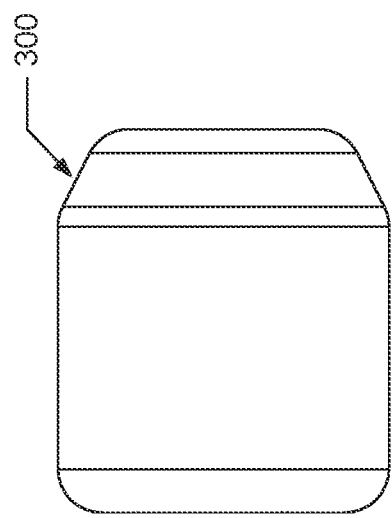
FIG. 8 is a back view of an exemplary attachment device, according to one embodiment of the present disclosure.

FIG. 8 is a back view of an attachment device 300, according to one embodiment.

Figure 9:
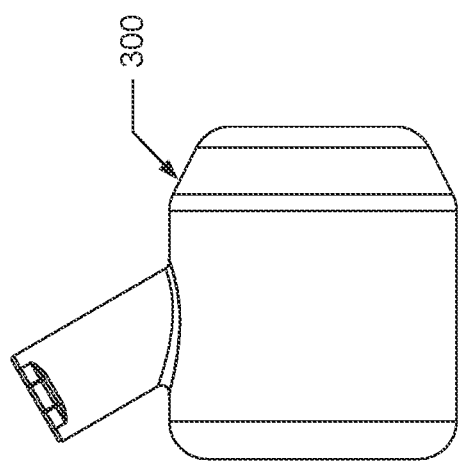
FIG. 9 is a left side view of an exemplary attachment device, according to one embodiment of the present disclosure.

FIG. 9 is a left side view of an attachment device 300, according to one embodiment.

Figure 10:
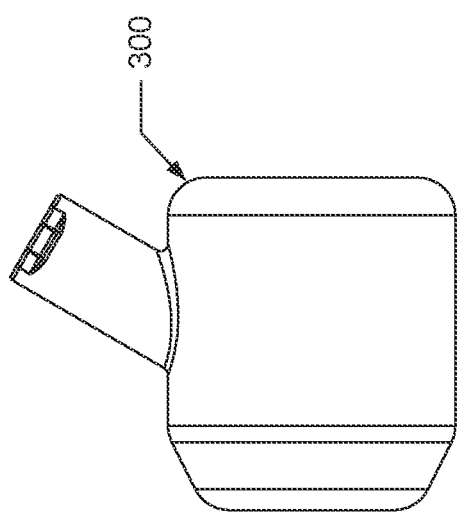
FIG. 10 is a right side view of an exemplary attachment device, according to one embodiment of the present disclosure.

FIG. 10 is a right side view of an attachment device 300, according to one embodiment.

FIG. 11 is a perspective view of an attachment device 1100, according to one embodiment. In at least one embodiment, the attachment device 1100 includes a central void 1102 through which a drainage device 100 (FIG. 1) or drainage device 301 (FIG. 3) is passed. According to one embodiment, the attachment device 1100 is fitted over the drainage device 301 in a manner substantially similar to the attachment device 300 (FIG. 3). In various embodiments, the attachment device 1100 includes one or more materials, including, but not limited to, biocompatible plastics that may not significantly compromise a quality fluid with which the plastics may contact.

In one or more embodiments, the attachment device 1100 includes inputs 1101A, 1101B. In various embodiments, the input 1101A is configured for receiving fluid from a first fluid source and the input 1101B is configured for receiving fluid from a second fluid source (fluid sources not shown). In at least one embodiment, the inputs 1101A, 1101B include luer-lock fittings and/or other standardized fittings for attachment to a fluid source, pump, or other device or apparatus. In some embodiments, the inputs 1101A, 1101B include one-way valves (not shown) for preventing backflow of fluids out of an outer lumen. According to one embodiment, the inputs 1101A, 1101B allow for multiple fluids to be transmitted to the drainage device 301. For example, a dilution fluid is transmitted through the input 1101A and to a first outer lumen 405A (FIG. 4) and a saline solution is transmitted through the input 1101B to a second outer lumen 405B (FIG. 4). In some embodiments, additional inputs are included for providing additional fluid types to the drainage device 301. In at least one embodiment, one or more instruments, such as sensors or other medical devices, are passed through the input 1101A or 1101B.

Figure 12A:
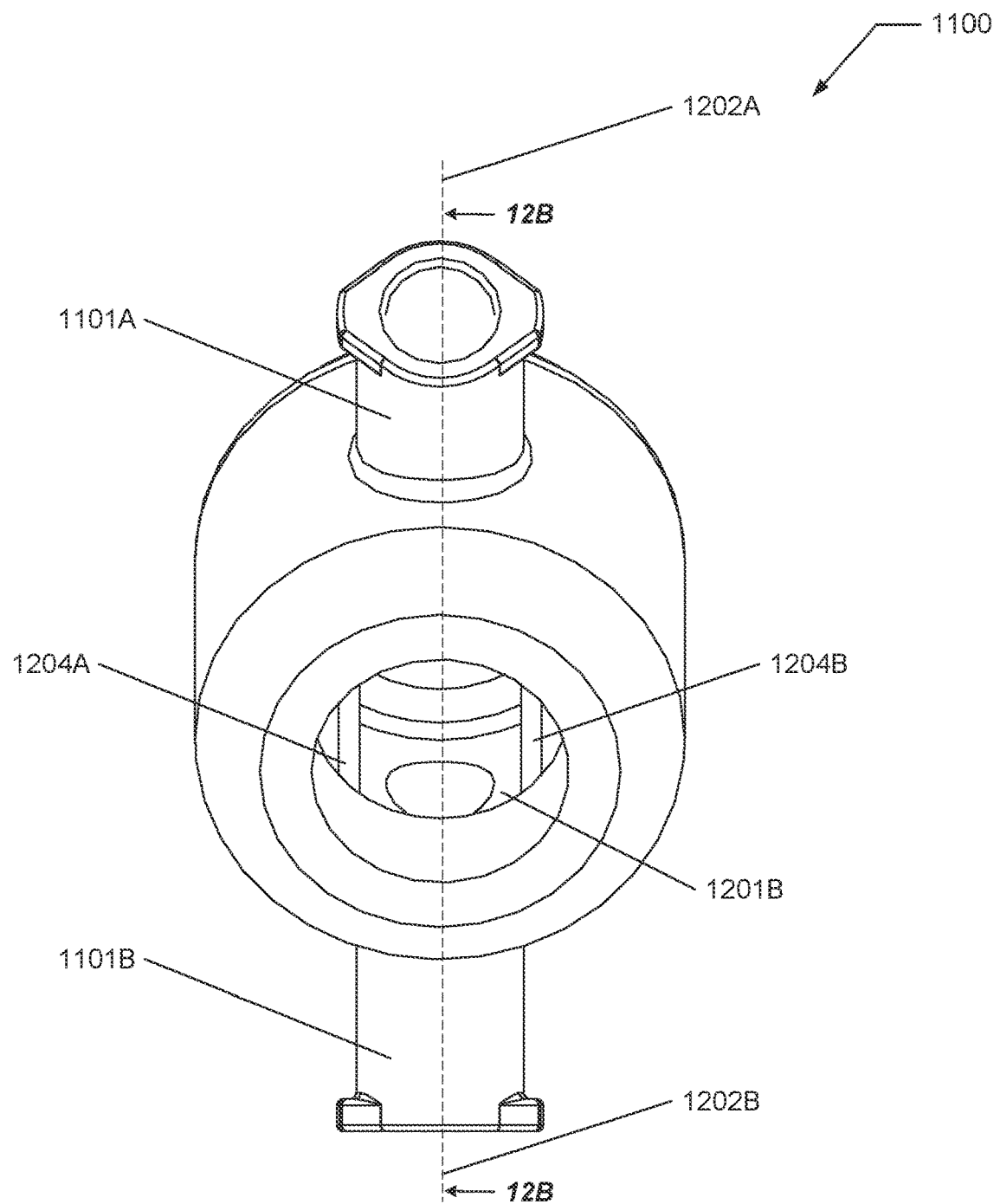
FIG. 12A is a top view of an exemplary attachment device, according to one embodiment of the present disclosure.
Figure 12B:
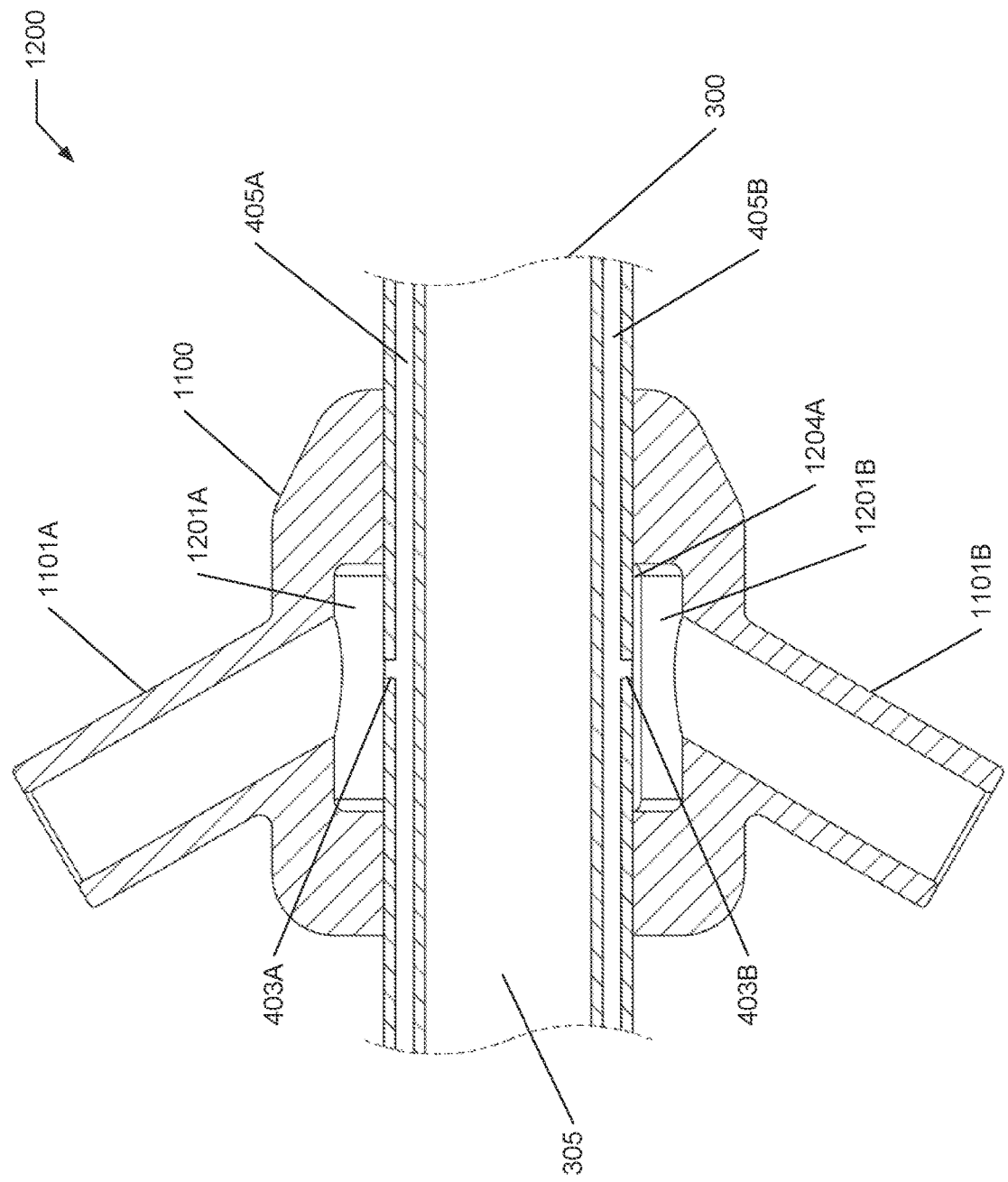
FIG. 12B is a cross-sectional view of an exemplary attachment device, according to one embodiment of the present disclosure.

FIG. 12A is a top view of an attachment device 1100. In one or more embodiments, a longitudinal axis 1202A, 1202B bisects the attachment device 1100 and defines a cross-section 1200 (FIG. 12B). In at least one embodiment, the attachment device 1100 includes one or more ribs 1204A, 1204B that divide a first chamber 1201A (see FIG. 12B) and a second chamber 1201B (see FIG. 12B), thereby maintaining the separation of the fluids from the input 1101A and input 1101B.

FIG. 12B is a cross-section 1200 of an attachment device 1100, according to one embodiment. In one or more embodiments, the input 1101A is configured to transmit fluid to a first chamber 1201A and the input 1101B is configured to transmit a second fluid to a second chamber 1201B that is separated from the first chamber 1201A. In at least one embodiment, the first chamber 1201A transmits the fluid through an inlet 403A and into a first outer lumen 405A, and the second chamber 1201B transmits the second fluid through a second inlet 403B to a second outer lumen 405B. In at least one embodiment, the attachment device 1100 allows for multiple fluids to be delivered to the drainage device 300 simultaneously or at various predetermined time periods. According to one embodiment, the rib 1204A separates the first chamber 1201A and the second chamber 1201B.

FIGS. 13-22 depict additional embodiments of the systems, devices, and methods discussed herein. For brevity, numbers previously used are used again in these figures to describe/show similar features and/or components.

Figure 13:
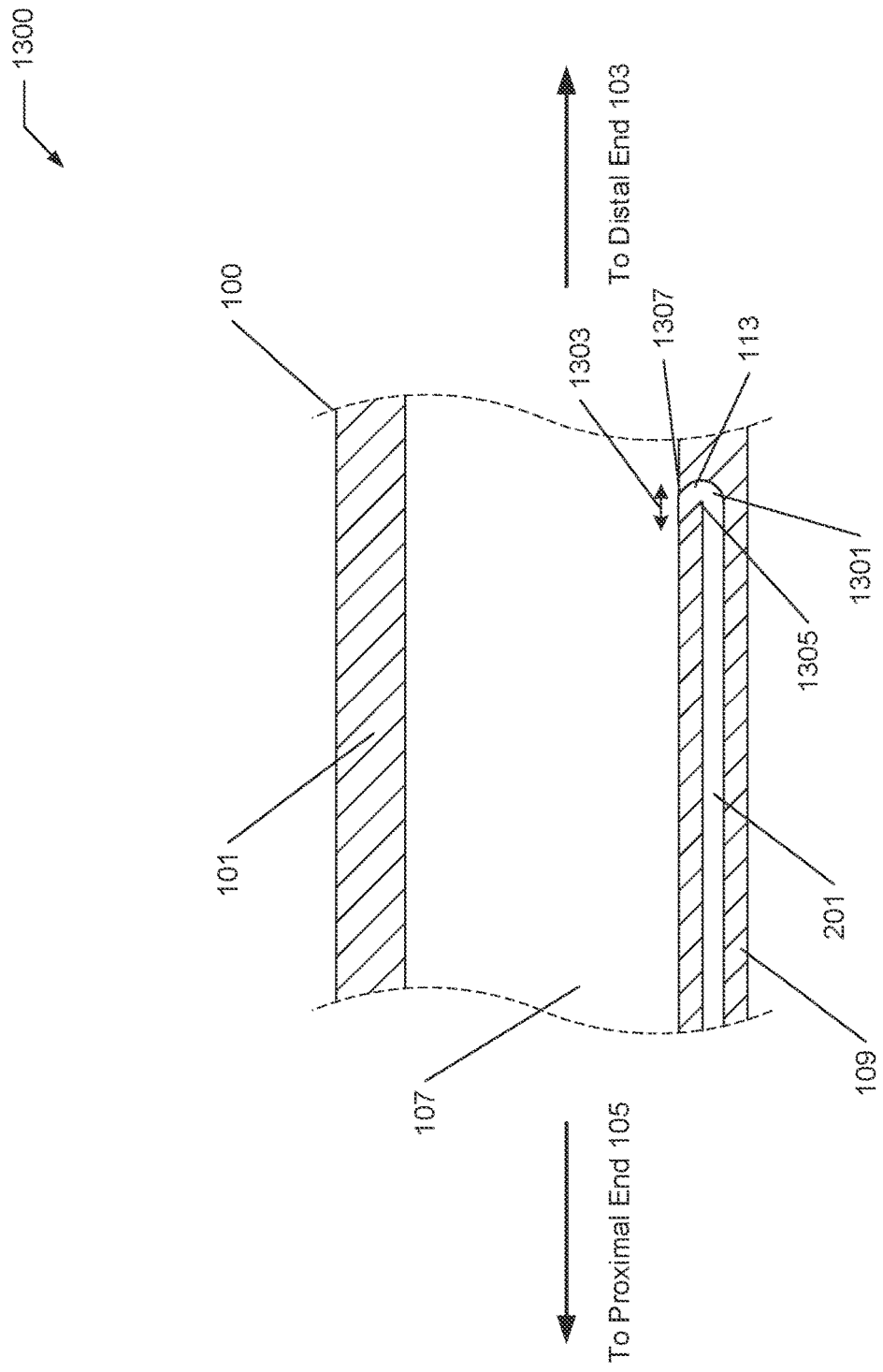
FIGS. 13-22 are cross-sectional views of exemplary drainage devices according to one embodiment of the present disclosure.

FIG. 13 is a partial cross-section 1300 of a drainage device (e.g., a drainage device 100), according to one embodiment. In at least one embodiment, the outer lumen 201 is connected to a port 113 such that fluid from the outer lumen 201 enters the inner lumen 107 via the port 113. In some embodiments, the outer lumen 201 includes a curved portion 1301 configured to direct the flow of fluid toward the proximal end 103. In at least one embodiment, the port 113 is angled toward the proximal end 103 (e.g., in an orientation opposite the flow of fluid from the distal end 103 and/or eyelets 111). In various embodiments, the curved portion 1301 and/or the angling of the port 113 reduces a potential of fluid from the inner lumen 107 flowing into the outer lumen 201, for example, in instances of pump and/or suction.

In some embodiments, the port 113 includes a diameter 1303 that measures about 0.01-10.0 mm, about 0.01-0.1 mm, about 0.1-1.0 mm, about 1.0-2.0 mm, about 2.0-3.0 mm, about 3.0-4.0 mm, about 4.0-5.0 mm, about 5.0-6.0 mm, about 6.0-7.0 mm, about 7.0-8.0 mm, about 8.0-9.0 mm, or about 9.0-10.0 mm. According to one embodiment, the diameter 1303 (or equivalent width dimension) tapers between a first end 1305 and a second end 1307 opposite the first end 1305. For example, the diameter 1303 decreases near the second end 1307 such that fluid passing through the port 113 experiences a Venturi effect that increases the velocity of the fluid as it exits the port 113. In at least one embodiment, an increased fluid velocity improves a rate of dilution and/or infusion of fluid passing through the inner lumen 107. In some embodiments, the port 113 includes a slit that occludes the port 113 below a predetermined pressure. In one example, upon saline being pumped through the outer lumen 201 above a predetermined flow rate, the pressure of the saline solution forces the slit open and the saline solution passes through the port 113. According to one embodiment, the slit is integrally formed with the port 113, for example, by reducing the diameter 1303 (or other equivalent width dimension) to provide the above-described functions.

Figure 14:
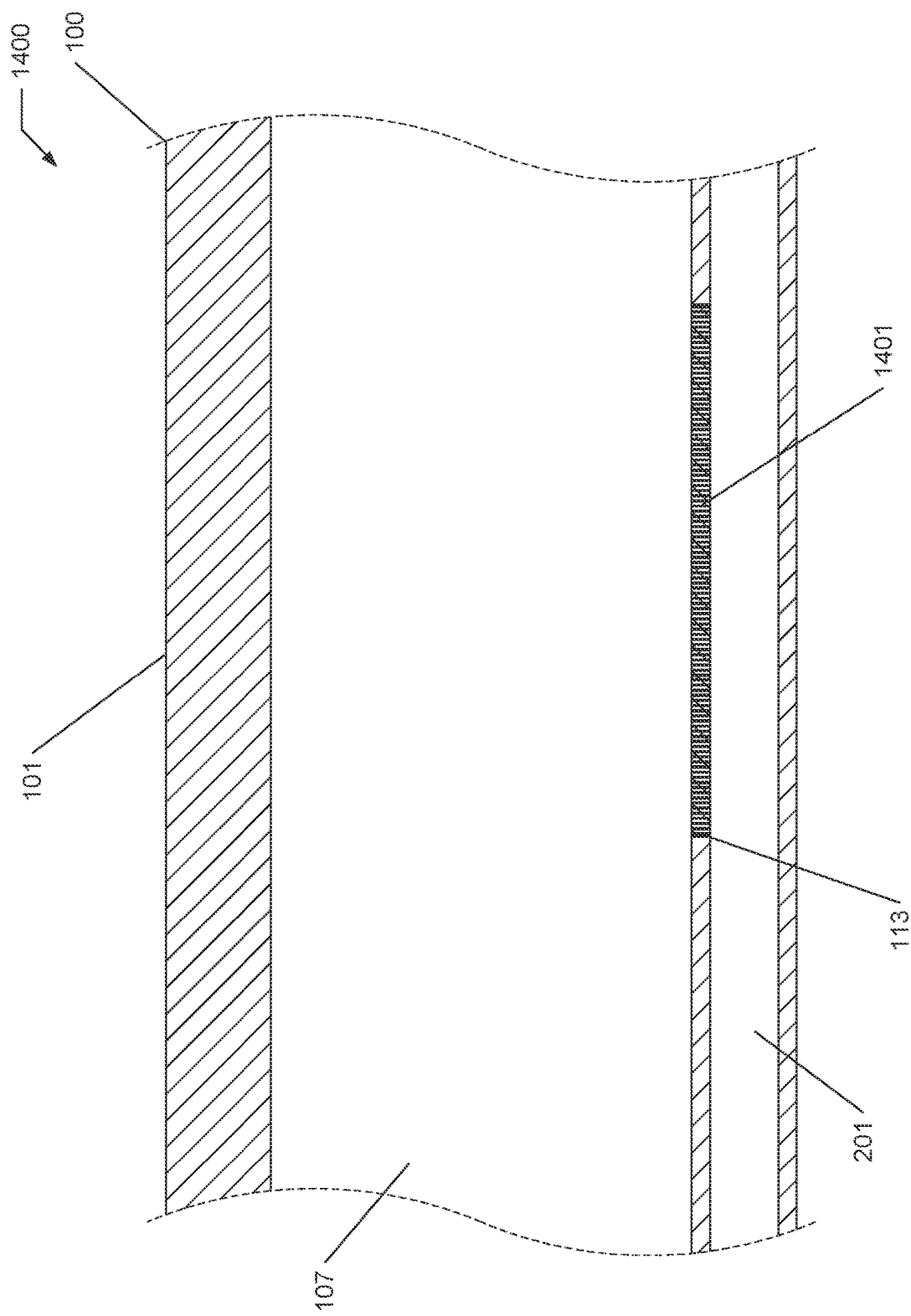

FIG. 14 is a partial cross-section 1400 of a drainage device 100, according to one embodiment. In one or more embodiments, the port 113 includes a membrane 1401. In some embodiments, the drainage device 100 includes a first subset and second subset of ports. According to one embodiment, the first subset of ports each include a membrane (e.g., membrane 1401) and a second subset of ports do not include a membrane. In at least one embodiment, the first subset of ports are connected to a first outer lumen (e.g., an outer lumen 201) and the second subset of ports are connected to a second outer lumen.

According to one embodiment, the membrane 1401 is selectively permeable such that fluid passing through the inner lumen 107 is not transmitted to the outer lumen 111, but fluid passing through the outer lumen 111 is transmitted through the membrane 1401 to the inner lumen 107. In at least one embodiment, the membrane 1401 is permeable upon a predetermined fluid pressure applied from the outer lumen 201 and/or upon generation of a predetermined pressure differential between the outer lumen 201 and the inner lumen 107. In some embodiments, the membrane 1401 includes one or more materials that are transmitted to the inner lumen 107 by the passing of the fluid from the outer lumen 111 and/or the inner lumen 107. In one example, the membrane 1401 is doped with an anticoagulant, such as heparin, that is transmitted to blood passing through the inner lumen 107. In this example, as saline from the outer lumen 201 passes through the membrane 1401, the saline picks up the anticoagulant and transmits the anticoagulant to the blood upon entering the inner lumen 107. In various embodiments, the membrane 1401 extends into the outer lumen 201 to increase saturation of fluid moving therethrough and/or to reduce a likelihood of the membrane 1401 becoming dislodged.

According to one embodiment, the membrane 1401 includes one or more materials, including, but not limited to, cotton, cellulose, and other suitable materials (e.g., that may withstand fabrication processes for forming the drainage device 100, or one or more elements thereof). In at least one embodiment, the one or more materials demonstrate flexibility properties similar to those demonstrated by materials included in the wall 109. In various embodiments, the membrane 1401 is manufactured separately from the drainage device 100 is installed therewithin during an assembly process.

In one or more embodiments, the membrane 1401 is doped by dissolving a doping material, such as heparin, in a carrier fluid that coats the membrane 1401 and is evaporated, thereby depositing the heparin. In some embodiments, the membrane 1401 is a restriction point to a fluid delivered from the outer lumen 201. In one example, the membrane 1401 includes layers of pores between the outer lumen 201 and the inner lumen 107. In this example, layers near the outer lumen 201 includes pores that are smaller in diameter than pores in layers near the inner lumen 107. Continuing this example, the differential pore sizes provide for even flow through the membrane 1401.

Figure 15:
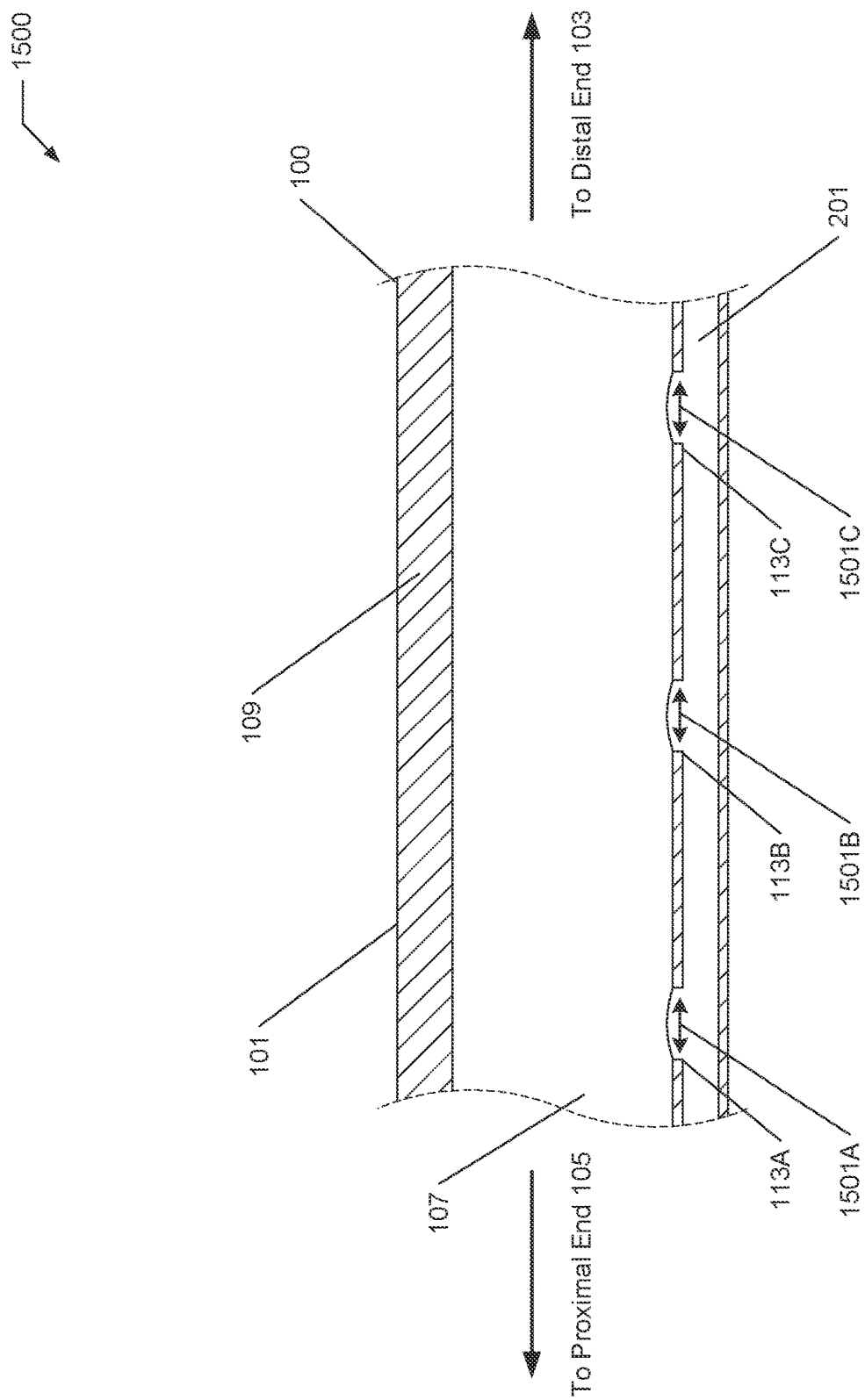

FIG. 15 is a partial cross-section 1500 of a drainage device 100, according to one embodiment. In various embodiments, the outer lumen 201 includes a plurality of ports 113A, 113B, 113C. It will be understood that the ports 113A, 113B, 113C are exemplary in nature and that greater or fewer numbers of ports 113 can be included in various embodiments of the drainage device 100. According to one embodiment, the ports 113A, 113B, 113C provide for dilution fluid distribution at multiple regions of the inner lumen 107. In some embodiments, the ports 113A, 113B, 113C allow for increased dilution of fluid flowing through the inner lumen 107 (e.g., as compared to dilution provide by a single port 113). In some embodiments, the increased capacity for dilution allows for a footprint of the drainage device 100 to be reduced, which may be desirable, for example, in instances where a target site is inaccessible to devices exceeding a particular width. For example, because the greater dilution reduces blockage formation, the diameter of the inner lumen 107 can be reduced, thereby reducing the footprint of the drainage device 100.

In some embodiments, the ports 113A, 113B, 113C are spaced equidistant along the outer lumen 201. In at least one embodiment, one or more of the ports 113A, 113B, 113C are arranged generally opposite to an eyelet (not shown) that is located on an opposing portion of the wall 109. In one example, the port 113A is located directly opposite from an eyelet 111 such that fluid exiting the port 113A is directed near fluid entering the eyelet 111. In various embodiments, the ports 113A, 113B, 113C include diameters 1501A, 1501B, 1501C that measure about 0.01-10.0 mm, about 0.01-0.1 mm, about 0.1-1.0 mm, about 1.0-2.0 mm, about 2.0-3.0 mm, about 3.0-4.0 mm, about 4.0-5.0 mm, about 5.0-6.0 mm, about 6.0-7.0 mm, about 7.0-8.0 mm, about 8.0-9.0 mm, or about 9.0-10.0 mm. In some embodiments, the diameters 1501A-C are substantially equal. In alternate embodiments, the diameters 1501A-C are selected to normalize the flow rate of fluid passing through the ports 113A, 113B, 113C. In one example, the diameters 1501A-C increase in magnitude near the distal end 103 such that a flow rate of fluid exiting the ports 113A, 113B, 113C is substantially similar. In some embodiments, the diameters 1501A-C are selected such that fluid passing through the port 113C exits at a peak flow rate compared to exiting flow rates associated with ports 113A, 113B. It will be appreciated that any combination of magnitudes of the diameters 1501A-C is contemplated for purposes including, but not limited to, providing equal exit flow rates, tapering exit flow rates, increasing exit flow rates, and other flow rate schemes.

Figure 16:
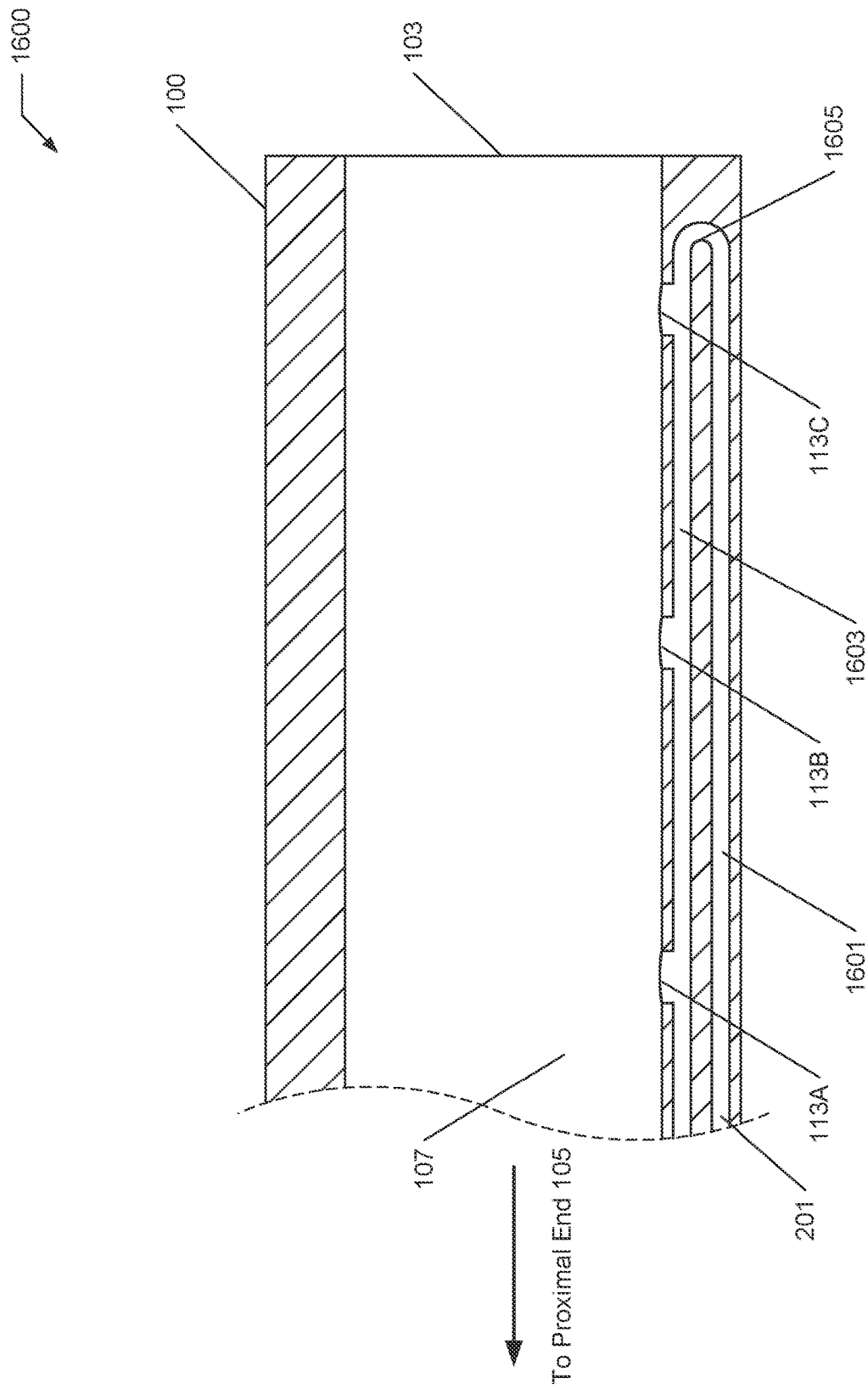

FIG. 16 is a partial cross-section 1600 of a drainage device 100, according to one embodiment. In various embodiments, the outer lumen 201 includes a first portion 1601, a second portion 1603, and a bend 1605 connecting the first portion 1601 to the second portion 1603. In one or more embodiments, a first portion of an outer lumen lies in a first plane and a second portion of an outer lumen lies in a second plane that is distinct from the first plane. In one example, a first portion of an outer lumen is oriented radially from a second portion of the outer lumen. In this example, a bend travelling radially in a wall (e.g., within which the outer lumen is formed) connects the first portion and the second portion).

According to one embodiment, dilution fluid flows from the first portion 1601 toward the distal end 103 and is redirected by the bend 1605 toward the proximal end 105 and through the second portion 1603. In one or more embodiments, the second portion 1603 includes ports 113A, 113B, and 113C through which dilution flows into the inner lumen 107. In various embodiments, the redirection of the fluid allows for a maximum flow rate to be demonstrated by fluid exiting nearest to the distal end 103. In at least one embodiment, the peak flow rate at the distal end 103 allows for immediate and maximal dilution of fluid, such as blood, entering the inner lumen 107 (e.g., as compared to dilution provided at ports 113 located nearer to the proximal end 105). In one example, the port 113C demonstrates a greater output flow rate compared to ports 113B, 113C. Continuing this example, the port 113C, being located nearest to the distal end 103, provides for an increased level of dilution to be provided immediately to blood entering the inner lumen 107. In at least one embodiment, dimensions of the ports 113A, 113B, 113C are additionally selected to complement or mitigate (e.g., normalize) the flow pattern of dilution fluid from the second portion 1603. It will be understood that the second portion 1603 may extend further along the length of the drainage device 100 near the proximal end 105 and that additional ports 113 may be connected thereto.

Figure 17:
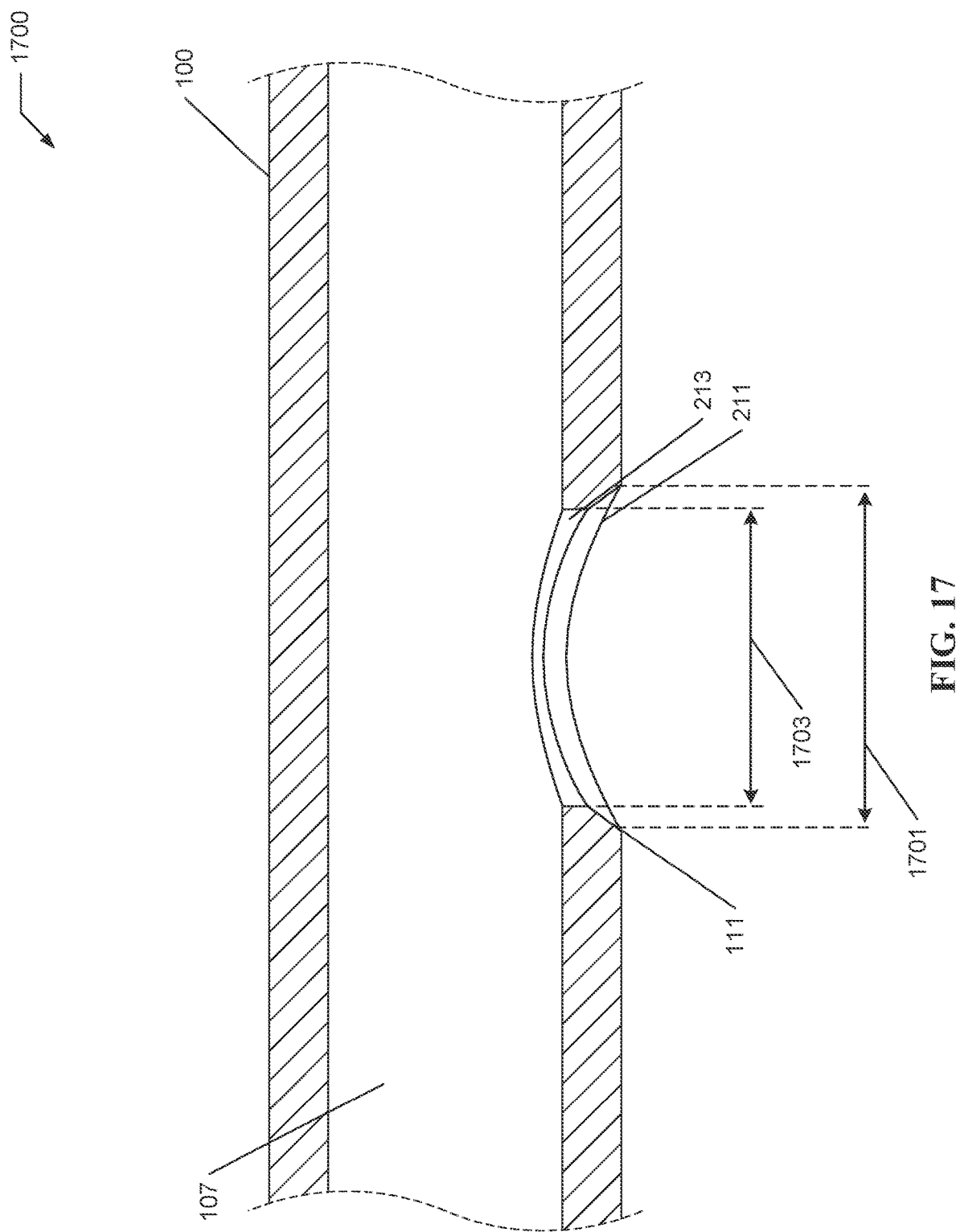

FIG. 17 is a partial cross-section 1700 of a drainage device 100, according to one embodiment. In one or more embodiments, the first opening 211 and second opening 213 of the eyelet 111 include a diameter and 1701 and a diameter 1703, respectively. In at least one embodiment, the diameter 1701 measures about 1-50 mm, about 1-5 mm, about 5-10 mm, about 10-15 mm, about 15-20 mm, about 20-25 mm, about 25-30 mm, about 30-35 mm, about 35-40 mm, about 40-45 mm, or about 45-50 mm. In various embodiments, the diameter 1703 measures about 1-50 mm, about 1-5 mm, about 5-10 mm, about 10-15 mm, about 15-20 mm, about 20-25 mm, about 25-30 mm, about 30-35 mm, about 35-40 mm, about 40-45 mm, or about 45-50 mm. According to one embodiment, the diameter 1701 is selected to exceed the diameter 1703 such that the eyelet 111 includes a generally funnel-like shape. In one example, the eyelet 111 includes tapering diameters in the region between the first opening 211 and second opening 213. In this example, with regard to the eyelet 111, the diameter 1701 is a maximum diameter and the diameter 1703 is a minimum diameter. Continuing this example, the tapering diameters provide for an increased surface area by which blood may enter the eyelet 111 and further provides for a Venturi effect that increases velocity of blood entering the eyelet 111 and moving through the inner lumen 107. In alternate embodiments, the diameter 1701 and diameter 1703 are substantially equal. According to one embodiment, the first opening 211 includes chamfered and/or rounded edges.

Figure 18:
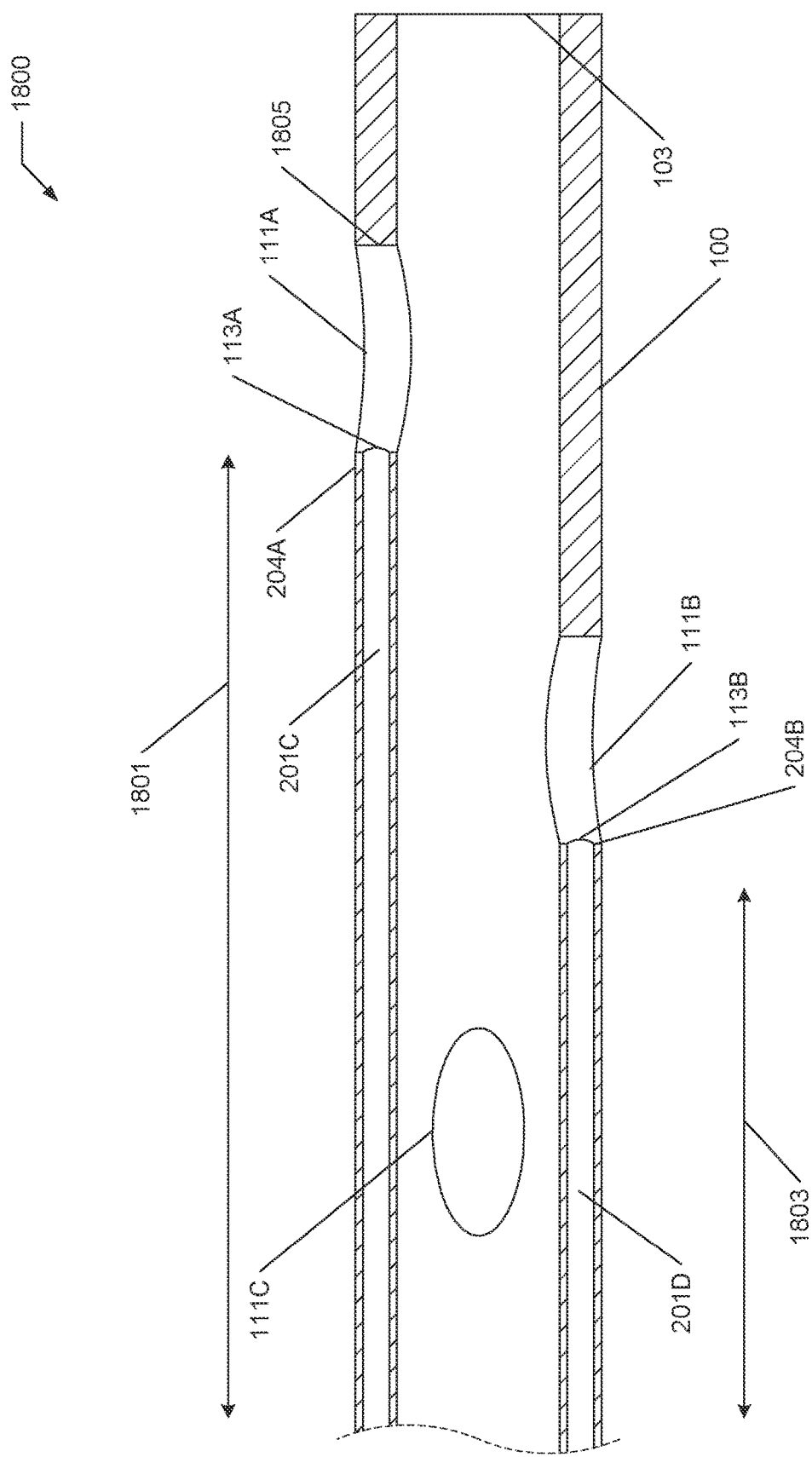

FIG. 18 is a partial cross-section 1800 of a drainage device 100, according to one embodiment. According to one embodiment, the drainage device 100 includes a first outer lumen 201C and a second outer lumen 201D. In various embodiments, each outer lumens 201C, 201D connects to an eyelet 111A, 111B, respectively. In one or more embodiments, the outer lumens 201C, 201D are connected to different fluid sources such that multiple fluids (or other substances or devices) may be provided to the inner lumen 107 and/or the environment external to the drainage device 100. In one example, the outer lumen 201C is connected to a dilution fluid source and the outer lumen 201D is connected to an antibacterial solution source or anticoagulant solution source. In at least one embodiment, the outer lumens 201C, 201D are connected to the same fluid source or to different fluid sources providing the same fluid.

In at least one embodiment, the outer lumen 201C connects to an eyelet 111A and the outer lumen 201D connects to an eyelet 111B at ports 113A, 113B, respectively. According to one embodiment, the outer lumen 201C includes a length 1801 and the outer lumen 201B includes a length 1803, each length being measured between an outer lumen proximal end 202 (see FIG. 2A) and an outer lumen distal end 204A, 204B. In various embodiments, the length 1801 and/or length 1803 measure about 1-250 cm, about 1-25 cm, about 25-50 cm, about 50-75 cm, about 75-100 cm, about 100-125 cm, about 125-150 cm, about 150-175 cm, or about 175-200 cm. In various embodiments, the outer lumen 201C and outer lumen 201D include different lengths. In one example, the length 1801 exceeds the length 1803, or vice versa.

In some embodiments, the outer lumen 201C includes a curve or angle, such as, for example, a bend 1605 (see FIG. 16) that redirects the flow of dilution fluid prior to entering the eyelet 111A. In one example, the outer lumen 201C includes a U-shaped bend that allows for dilution fluid to enter the eyelet 111A at a region 1805 that is located near the distal end 103. In some embodiments, the outer lumen 201C surrounds the eyelet 111A such that the dilution fluid enters the eyelet 111A at multiple points. In one example, the outer lumen 201C connects to multiple ports (e.g., 1-10 ports) that are arranged radially such that dilution fluid enters the eyelet 111A from multiple points forming a generally radial pattern of distribution. In this example, the ports are arranged radially (e.g., from 0 to 360 degrees) to promote equal and maximal fluid distribution.

Figure 19:
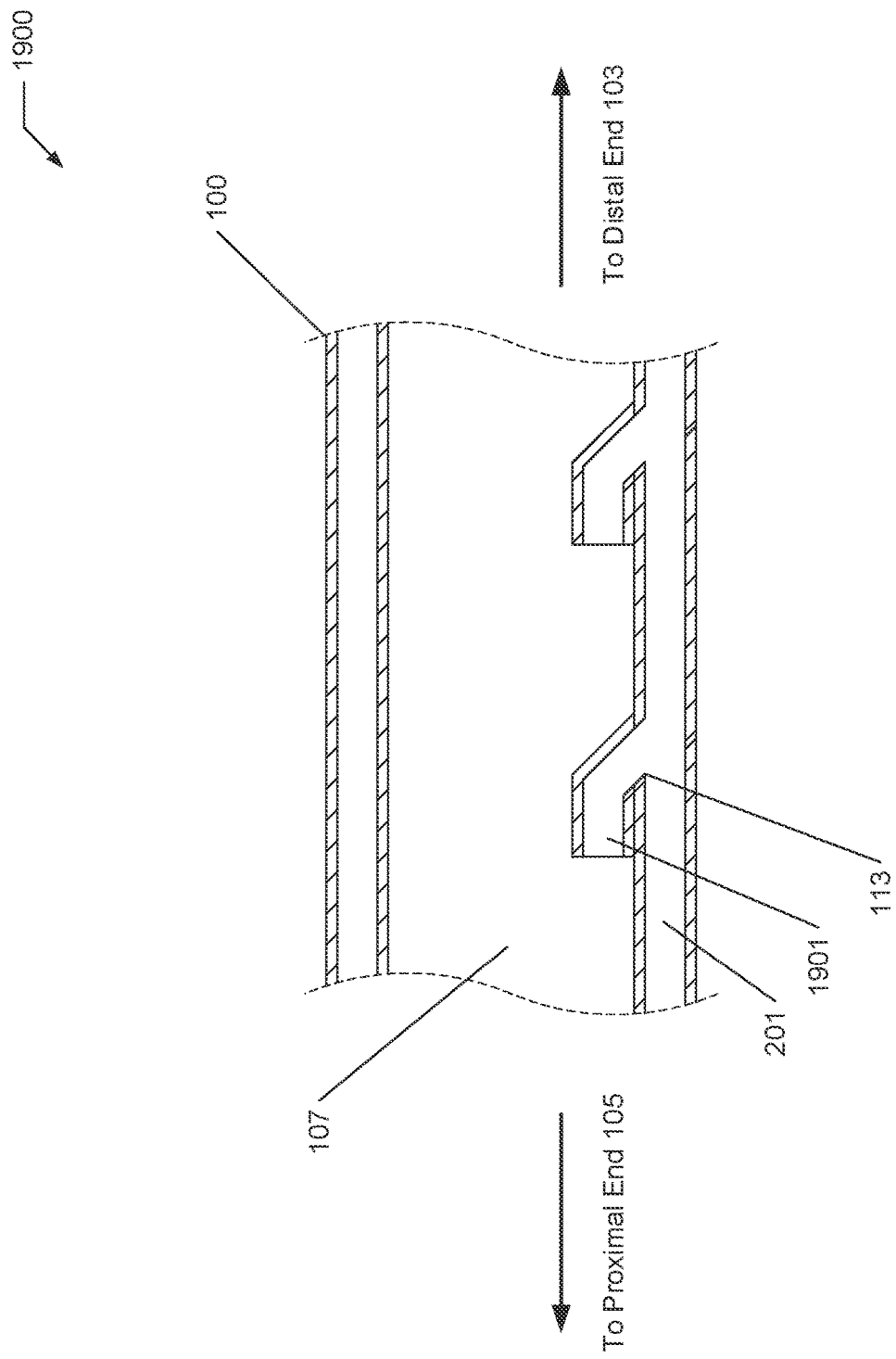

FIG. 19 is a partial cross-section 1900 of a drainage device 100, according to one embodiment. In some embodiments, the outer lumen 201 is connected to one or more protrusions 1901 that project into the inner lumen 107. In at least one embodiment, the protrusion 1901 includes an outlet 1903 oriented towards the proximal end 105. According to one embodiment, the protrusion 1901 includes a low profile shape configured to minimize impedance to the flow of fluid through the inner lumen 107. In one example, a section of the protrusion 1901 near the distal end 103 is sloped away from the distal end 103 to reduce the impedance to the fluid flow.

Figure 20:
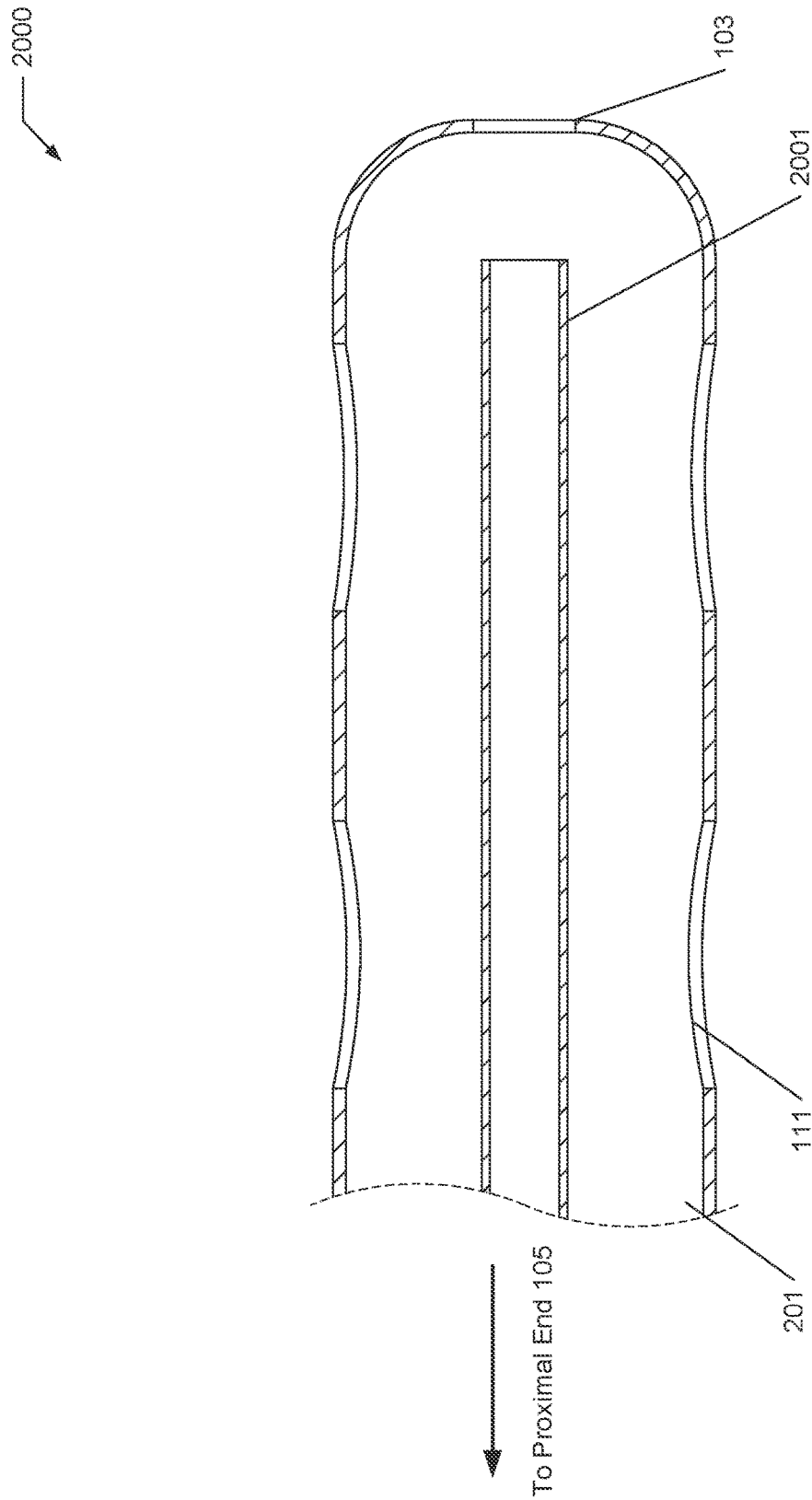

FIG. 20 is a partial cross-section 2000 of a drainage device 100, according to one embodiment. In various embodiments, the drainage device 100 includes the outer lumen 201 and a plurality of eyelets 111 through which fluids from an external environment enter the outer lumen 201. In at least one embodiment, the fluids also enter the outer lumen 201 through the distal end 103. According to one embodiment, a vacuum source is connected to the outer lumen 201 such that fluid entering the eyelets 111 is drawn through the outer lumen 201 and toward the proximal end 105. In various embodiments, the drainage device 100 includes an inner lumen 2001 that opens into the outer lumen 201. According to one embodiment, the inner lumen 2001 is connected to a fluid source and dilution fluid, and/or other fluids, therefrom is drawn (and/or pumped) through the inner lumen 2001 and into the outer lumen 201. In one example, the vacuum source creates a negative pressure in the outer lumen 201 that draws in blood through the distal end 103 and eyelets 103, and also draws dilution fluid from the inner lumen 2001 into the outer lumen 201, thereby potentially reducing or preventing clotting processes occurring in the drained blood.

Figure 21:
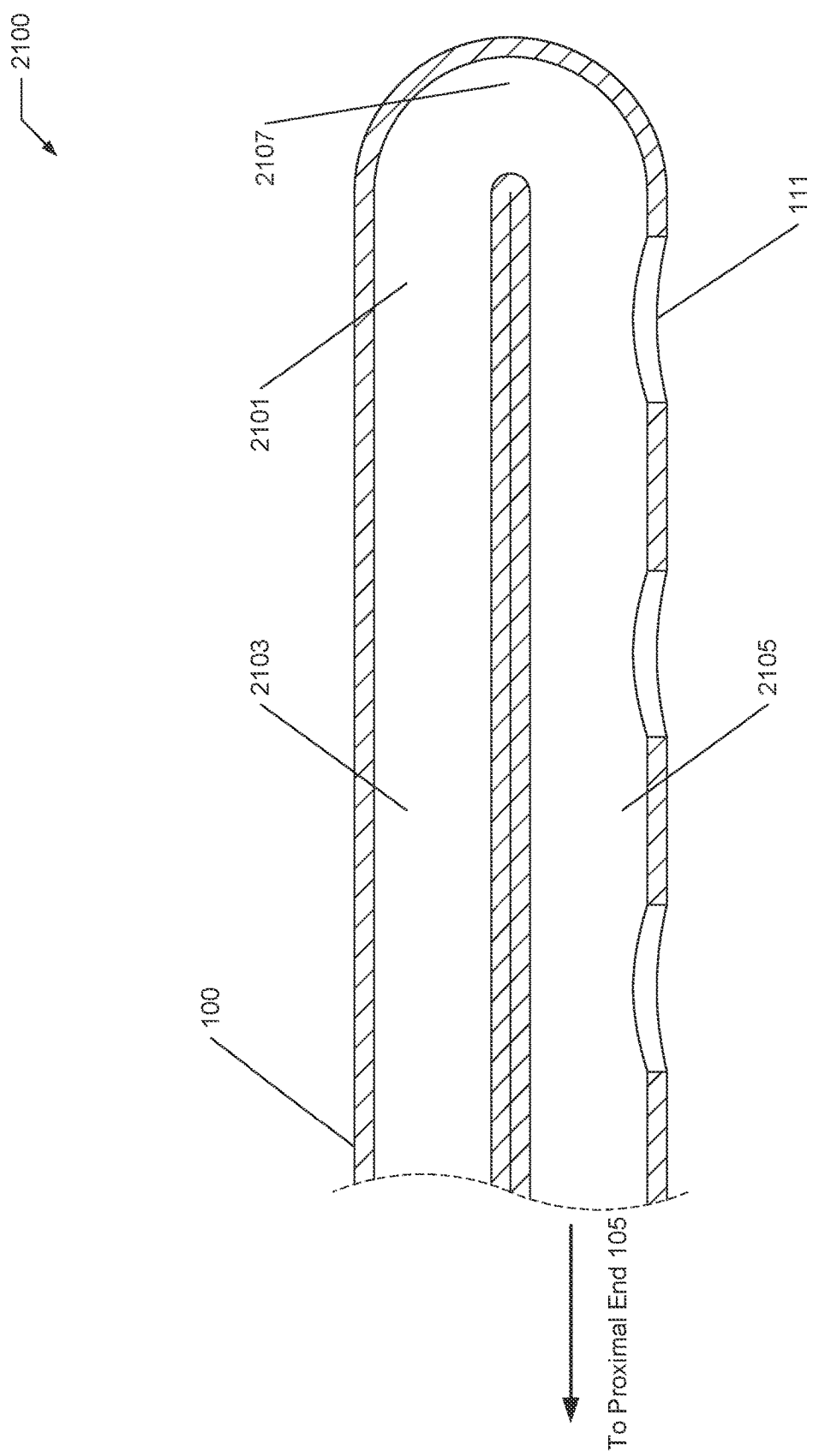

FIG. 21 is a partial cross-section 2100 of a drainage device 100, according to one embodiment. According to one embodiment, the drainage device 100 includes an inner lumen 2101 including a first portion 2103 and a second portion 2105 that are connected by a bend 2107. In at least one embodiment, the first portion 2103 is connected to a fluid source (not shown) and the second portion 2103 is connected to a vacuum source (not shown). In various embodiments, the vacuum source generates a negative pressure in the inner lumen 2101 such that fluids external to the drainage device 100 are drained through one or more eyelets 111 into the second portion 2105. In one or more embodiments, the negative pressure draws dilution fluid from the fluid source into the first portion 2103 and through the second portion 2105, thereby mixing the dilution fluid with the incoming external fluid. In one example, blood entering the second portion 2105 is diluted by fluid from the first portion 2103 such that clotting processes occurring in the blood are reduced or prevented.

Figure 22:
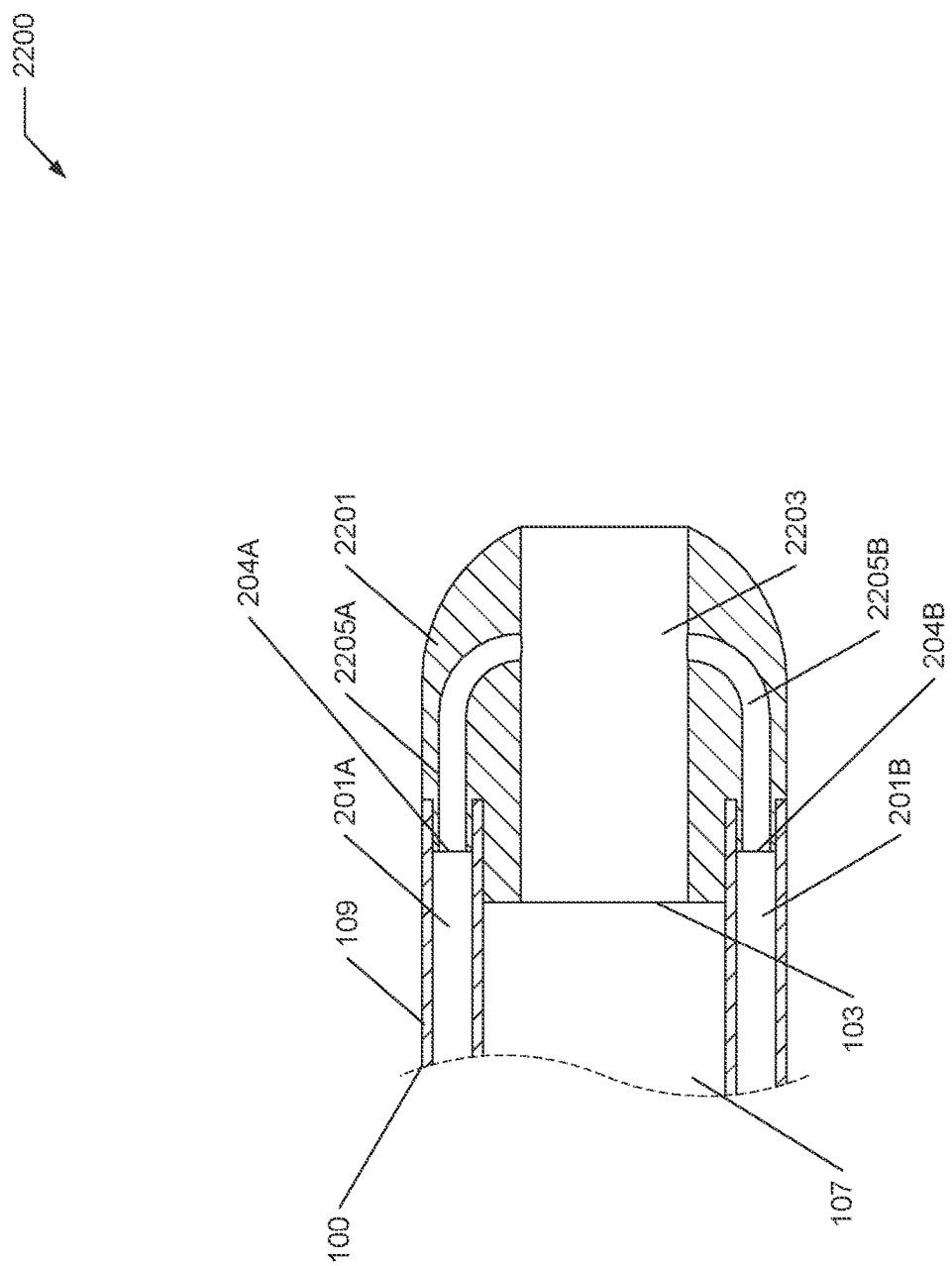

FIG. 22 is a partial cross-section 2200 of a drainage device 100, according to one embodiment. In various embodiments, the cap 2201 is press-fit, glue, or otherwise attached to the drainage device 100. In some embodiments, a cap 2201 is attached to the distal end 103. In one or more embodiments, the cap 2201 is sized to preserve a low profile of the drainage device 100. In at least one embodiment, the cap 2201 includes a central portion 2203 and side portions 2205A, 2205B. In various embodiments, the central portion 2203 is sized to be received into and substantially conform to the inner lumen 107, and the side portions 2205A, 2205B are sized to be received into and substantially conform to the outer lumens 201A, 201B, respectively. In at least one embodiment, the central portion 2203 is open at a distal end 2207 and a proximal end 2209 such that fluid external to the drainage device 100 may pass through the central portion 2203 and into the inner lumen 107. In various embodiments, from the outer lumens 201A, 201B, dilution fluid enters the corresponding side portions 2205A, 2205B, is directed into the central portion 2203, and exits from the cap 2201 into the inner lumen 107.

The following paragraph provides exemplary description of various alternate embodiments of the drainage device 100 shown in FIG. 22. In one or more embodiments, prior to insertion of the cap 2201, the inner lumen 107 and outer lumens 201A, 201B are open at the distal end 103 and distal ends 204A, 204B. In various embodiments, the central portion 2203 is closed at the distal end 2207 and proximal end 2209, thereby occluding the inner lumen 107 at the distal end 103. According to one embodiment, the side portions 2205A, 2205B occlude the outer lumens 201A, 201B at the distal ends 204A, 204B. In at least one embodiment, fluid external to the drainage device 100 enters the lumen 107 via one or more eyelets (not shown, see FIG. 1) and fluid from the outer lumen 201 enters the inner lumen 107 via the one or more eyelets 111 and/or from one or more ports (not shown, see FIG. 1). Thus, in some embodiments, insertion of the cap 2201 configures the drainage device 100 such that external fluids may be drained and diluted simultaneously.

As will be understood, the various embodiments discussed herein are not mutually exclusive, even if discussed separately. Different features and components discussed herein may be used together or separately. For example, the cap features of FIG. 22 could be combined with other features of the devices discussed herein, such as, for example, the features shown in FIG. 19.

Figure 23:
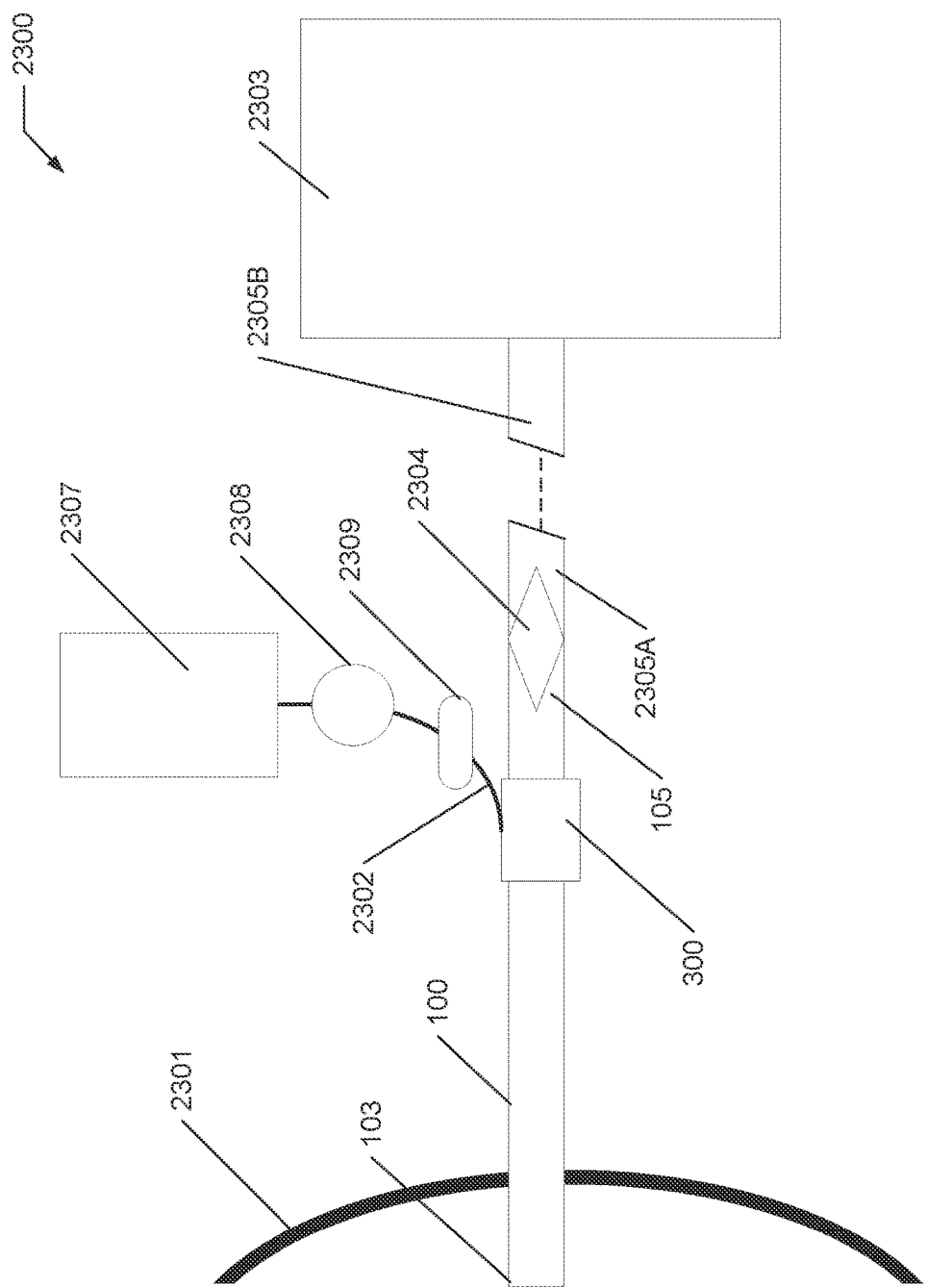
FIG. 23 is a diagram of an exemplary drainage system, according to one embodiment of the present disclosure.

FIG. 23 is a diagram of an exemplary drainage system 2300 according to one embodiment of the present disclosure. As will be understood and appreciated, the exemplary drainage system 2300 shown in FIG. 23 represents merely one approach or embodiment of the present system, and other aspects are used according to various embodiments of the present system.

In various embodiments, the drainage system 2300 includes, but is not limited to, a drainage device 100, an attachment mechanism 300, a vacuum source 2303, and a fluid source 2307. In at least one embodiment, a distal end 103 of the drainage device 100 is inserted into a target site 2301, such as, for example, a chest cavity. In various embodiments, the vacuum source 2303 generates a negative pressure within the drainage device 100 (e.g., within an inner lumen 107) and a drainage tube 2305A, 2305B. The vacuum source 2303 may operate linearly and in a continuous manner or may operate in a variable manner (e.g., generating varying levels of negative pressure). According to one embodiment, at the proximal end 105 of the drainage device 100 a connector 2304 connects a drainage tube 2305A such that fluid from the drainage device 100 may pass into and through the drainage tube 2305A. In one or more embodiments, the fluid may pass through the drainage tube 2305A to a second portion of drainage tube 2305B and into a collection canister of the vacuum source 2303.

According to one embodiment, via the attachment mechanism 300, the fluid source 2307 is configured to transmit one or more fluids through tubing 2302 and into the attachment device 300, which transmits the fluid to the drainage device 100 (e.g., to an outer lumen 201). In at least one embodiment, the one or more fluids include, but are not limited to, dilution fluids, such as a heparin solution, saline, contrast agents, and pharmaceuticals. In some embodiments, gravity and/or the negative pressure from the vacuum source 2303 draws the fluid into the drainage device 100. In one or more embodiments, a pump 2308 generates a positive pressure that pumps the fluid into the drainage device 100. In various embodiments, the pressure is a bolus, a continuous pressure, or a combination thereof. According to one embodiment, the pressure is not limited to peristaltic action. In at least one embodiment, the tubing 2302 includes a valve 2309 for controlling the flow of the fluid. According to one embodiment, the valve 2309 is a one-way valve that prevents the fluid from draining of the drainage device 100, for example, in instances in which the drainage device 100 is disconnected from the fluid source 2307.

Figure 24:
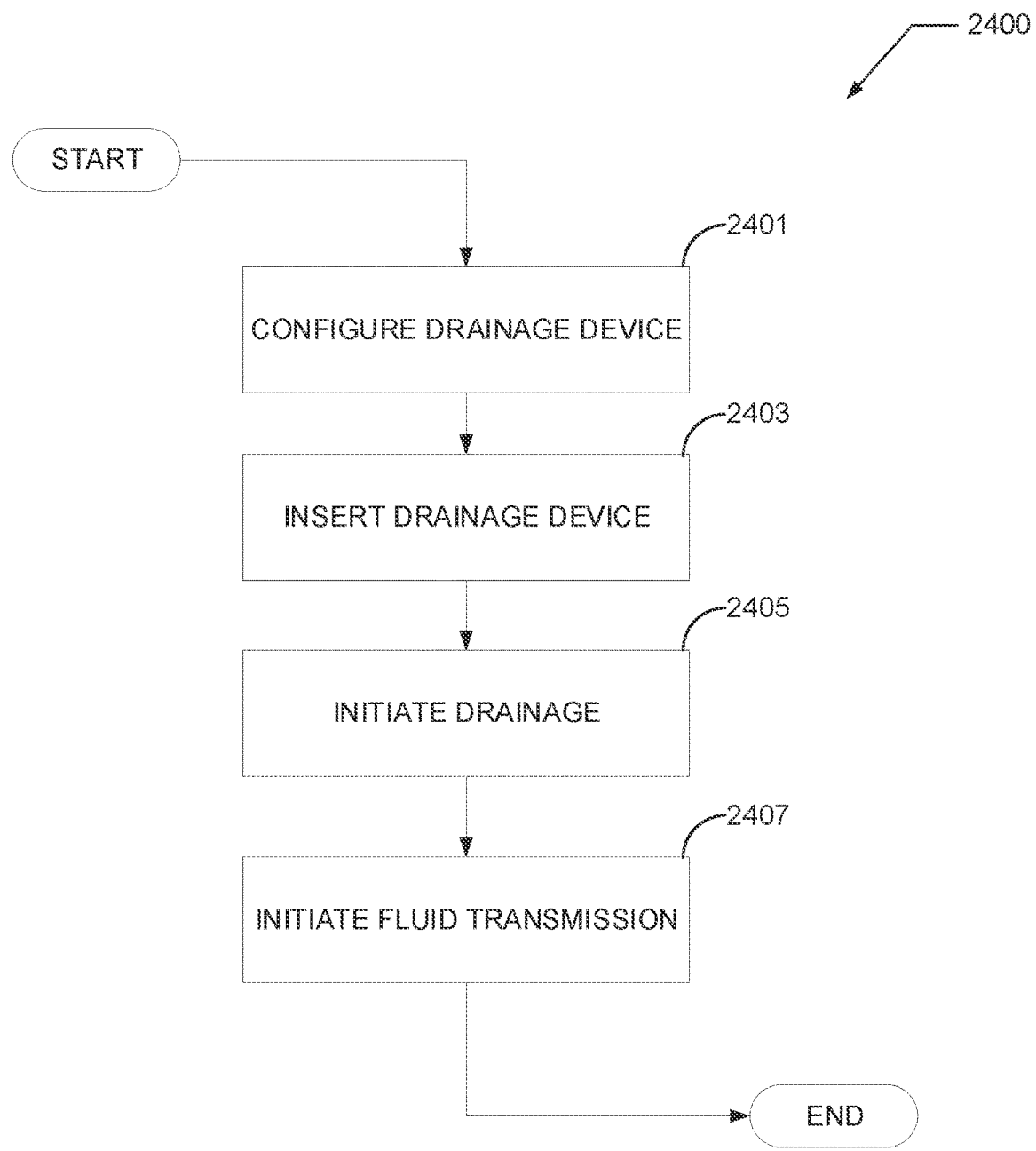
FIG. 24 is a flowchart of an exemplary drainage process, according to one embodiment of the present disclosure.

FIG. 24 is a flowchart of an exemplary drainage process 2400 according to one embodiment of the present disclosure. As will be understood by one having ordinary skill in the art, the steps and processes shown in FIG. 24 (and those of all other flowcharts and sequence diagrams shown and described herein) may operate concurrently and continuously, are generally asynchronous and independent, and are not necessarily performed in the order shown.

At step 2401, a drainage device 100 is configured. In various embodiments, configuring the drainage device 100 includes connecting a drainage device (e.g., a drainage device 100 as shown in FIG. 1) to various elements of a drainage system 2300. In one example, the attachment device 300 is connected near a distal end 103 of the drainage device. In some embodiments, the drainage device is provided with the attachment device 1300 connected near the distal end. In another example, a first end of tubing 2302 is connected to an input of an attachment device (e.g., an attachment device 300 as shown in FIG. 3) and a second end of the tubing 2302 is connected to a fluid source. In this same example, a proximal end of the drainage device and a drainage tube are connected to a connector, and a second end of the drainage tube is connected to a vacuum source. In at least one embodiment, the drainage device is flushed with a syringe or other fluid source. For example, a fluid source 2307 (see FIG. 23) is connected to the inner lumen and/or outer lumen of the drainage and is activated to flush the one or more lumens with a saline solution and clear any potential blockages therein.

At step 2403, the drainage device is inserted to a target site. In at least one embodiment, the drainage device is inserted to a predetermined depth at the target site. Non-limiting examples of the target site include, but are not limited to, chest cavities, intercostal spaces, and other body cavities including fluid for which drainage is desired, as well as seromas, abscesses, cysts, hematomas. In some embodiments, the drainage device is inserted to a target site prior to being connected to the vacuum source and/or fluid source.

At step 2405, drainage is initiated. According to one embodiment, the drainage of fluid from the target site initiates upon insertion of the drainage device. In some embodiments, drainage is initiated by activation of the vacuum source. In one or more embodiments, upon drainage initiation, fluid at the target site is drawn into and through the drainage device to the vacuum source (e.g., into a collection canister). In at least one embodiment, the drainage is maintained at a predetermined flow rate, pressure, and/or time period. In various embodiments, the predetermined flow rate is about 0.1-3.0 L/hr., about 0.1-1.0 L/hr., about 1.0-1.5 L/hr., about 1.5-2.0 L/hr., about 2.0-2.5 L/hr., or about 2.5-3.0 L/hr. According to one embodiment, the predetermined pressure is about 0.1-100 cm $H_2O$, about 0.1-10 cm $H_2O$, about 10-20 cm $H_2O$, about 20-30 cm $H_2O$, about 30-40 cm $H_2O$, about 40-50 cm $H_2O$, about 50-60 cm $H_2O$, about 60-70 cm $H_2O$, about 70-80 cm $H_2O$, about 80-90 cm $H_2O$, or about 90-100 cm $H_2O$. In one or more embodiments, the predetermined time period is about 1 hour, about 1 day, about 1 week, 1 month, 1 year (e.g., as may be utilized in indwelling chest tubes), or other suitable time periods.

At step 2407, fluid transmission is initiated. In some embodiments, a valve at the fluid source is opened allowing fluid to flow into the drainage device via the attachment mechanism. In various embodiments, a pump activates and drives the fluid into the drainage device. In at least one embodiment, the fluid transmission is performed at a predetermined flow rate to provide a predetermined mixing ratio to fluid from the target site that enters the drainage device. In one or more embodiments, the predetermined flow rate is about 0.001-2.0 L/hr., about 0.001-0.01 L/hr., about 0.01-0.05 L/hr., about 0.05-0.1 L/hr., about 0.1-1.0 L/hr., or about 1.0-2.0 L/hr. In various embodiments, the predetermined mixing ratio of external fluid to fluid from the outer lumen (e.g., which may be a dilution ratio in some embodiments) is about 100:1, about 50:1, about 25:10, about 10:1, about 5:1, or about 2:1, about 1:1, about 1:10, about 1:100, about 1:1000, or about 1:10000. In at least one embodiment, the fluid transmission proceeds for a predetermined time period, which may be equivalent to the predetermined time period of drainage activation or may correspond to a second predetermined time period that is less than the period of drainage activation.

While various aspects have been described in the context of a preferred embodiment, additional aspects, features, and processes of the claimed devices, systems, and methods will be readily discernible from the description herein, by those of ordinary skill in the art. Many embodiments and adaptations of the disclosure and claimed devices, systems, and methods other than those herein described, as well as many variations, modifications, and equivalent arrangements and processes, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed devices, systems, and methods. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed devices, systems, and methods. In addition, some steps may be carried out simultaneously, contemporaneously, or in synchronization with other steps.

The embodiments were chosen and described in order to explain the principles of the claimed devices, systems, and methods and their practical application so as to enable others skilled in the art to utilize the devices, systems, and methods and various embodiments and with various modifications as are suited to the particular use contemplated. Alternative embodiments will become apparent to those skilled in the art to which the claimed devices, systems, and methods pertain without departing from their spirit and scope. Accordingly, the scope of the claimed devices, systems, and methods is defined by the appended claims rather than the foregoing description and the exemplary embodiments described therein.

What is claimed is:

1. A blockage resistant drainage device comprising:
   a cylindrical body forming a longitudinal axis between a proximal end and a distal end;
   an inner lumen formed within the cylindrical body and comprising a particular diameter;
   a plurality of outer lumens formed within the cylindrical body, each of the plurality of outer lumens comprising a diameter of between 0.1 mm to a diameter equal to the particular diameter for passing dilution fluid to the inner lumen; and
   a plurality of eyelets extending from an exterior surface of the cylindrical body to the inner lumen for draining fluid from a patient, each of the plurality of eyelets comprising:
      a first opening at the exterior surface comprising a diameter of about 1-50 mm; and
      a second opening at a point of entry of the inner lumen, wherein a diameter of the second opening is smaller than a diameter of the first opening.

2. The blockage resistant drainage device of claim 1, wherein each of the plurality of outer lumens pass dilution fluid into the inner lumen at a point adjacent to an eyelet of the plurality of eyelets.

3. The blockage resistant drainage device of claim 1, wherein:
   the plurality of eyelets comprise a distal eyelet proximate the distal end of the cylindrical body; and
   each of the plurality of outer lumens pass dilution fluid into the inner lumen through an opening located at a point between the distal end of the cylindrical body and the distal eyelet.

4. The blockage resistant drainage device of claim 1, wherein:
   the distal end of the cylindrical tube is sealed;
   the inner lumen and at least one outer lumen of the plurality of outer lumens are fluidly connected near the distal end of the cylindrical tube; and
   the at least one outer lumen passes dilution fluid to the inner lumen near the distal end of the cylindrical tube.

5. The blockage resistant drainage device of claim 1, wherein the blockage resistant drainage device comprises a cap attached to a distal end of the cylindrical body.

6. The blockage resistant drainage device of claim 5, wherein the cap comprises a cap lumen connecting the outer lumen and the inner lumen such that the dilution fluid passes through the outer lumen and the cap lumen and into the inner lumen.

7. The blockage resistant drainage device of claim 1, wherein the inner lumen is configured to be operatively connected to a vacuum system.

8. The blockage resistant drainage device of claim 1, wherein the blockage resistant drainage device further comprises a luer lock comprising a one-way valve at the point near the proximal end for connecting at least one of the plurality of outer lumens to a mechanism for delivering dilution fluid to the inner lumen.

9. The blockage resistant drainage device of claim 8, wherein the mechanism for delivering dilution fluid comprises a pump for pumping the dilution fluid.

10. The blockage resistant drainage device of claim 8, wherein the mechanism for delivering dilution fluid comprises a syringe for pushing the dilution fluid.

* * * * *